United States Patent [19]

Zipplies et al.

[11] Patent Number: 4,935,426
[45] Date of Patent: Jun. 19, 1990

[54] N,N'-DISUBSTITUTED PIPERAZINES

[75] Inventors: Matthias Zipplies, Hirschberg; Hubert Sauter, Mannheim; Franz Roehl, Ludwigshafen; Thomas Kuekenhoehner, Frankenthal; Lothar Janitschke, Kleinniedesheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 307,525

[22] Filed: Feb. 8, 1989

[30] Foreign Application Priority Data

Feb. 9, 1988 [DE] Fed. Rep. of Germany ....... 3803860

[51] Int. Cl.$^5$ ................. A61K 31/495; C07D 295/02; C07D 295/06; C07D 295/08; C07D 407/06; C07D 409/06
[52] U.S. Cl. ..................................... 514/255; 514/252; 544/229; 544/230; 544/359; 544/367; 544/369; 544/374; 544/379; 544/392; 544/394; 544/395; 544/398; 544/401
[58] Field of Search ............... 544/230, 379, 381, 392, 544/394, 395, 229, 359, 367, 369, 374, 398, 401; 514/252, 255

[56] References Cited

U.S. PATENT DOCUMENTS 2,927,924  3/1960  Mills ..................................... 544/360
3,941,789  3/1976  Renth et al. ........................ 544/360
4,523,014  6/1985  Loev et al. .......................... 544/386

FOREIGN PATENT DOCUMENTS 227269   5/1963  Austria .
1108226  6/1961  Fed. Rep. of Germany .
2727482  1/1979  Fed. Rep. of Germany .
998509  11/1961 United Kingdom .

OTHER PUBLICATIONS

Renth et al., Chem. Abst. 77-34573u (1972).
Renth et al., Chem. Abst. 81-120691 S (1974).
Maffrand et al., Chem. Abst. 86-43741 k (1977).
Verpe et al., Chem. Abst. 88-62415 q (1978).
Nesvadba et al., Chem. Abst. 92-41990 z (1980).

Primary Examiner—Cecilia Shen
Attorney, Agent, or Firm—Oblon, Spivak, McClelland, Maier & Neustadt

[57] ABSTRACT

N,N'-disubstituted piperazines of the general formula I

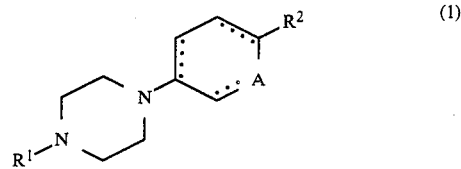

where the group ---- is unsaturated (═) or saturated (—) and the substituents $R^1$, $R^2$ and A have the following meanings:

A is —, —CH═, —CH$_2$—, —CH$_2$—CH$_2$—, $R^1$ is alkyl, alkenyl, alkynyl, cycloalkyl, cycloalkenyl, alkylcycloalkyl, cycloalkenylalkyl, alkylcycloalkenyl, bicycloalkyl, bicycloalkylalkyl or alkylbicycloalkyl, these radicals being unsubstituted or substituted by hydroxy, halogen, alkoxy or trialkylsilyl, $R^1$ is further heterocycloalkyl with oxygen and/or sulfur, heterocycloalkylmethyl with oxygen and/or sulfur, alkyl-substituted heterocycloalkylmethyl with oxygen and/or sulfur, and $R^2$ is alkyl, alkoxy, trimethylsilyl, cycloalkyl, alkylthio, and plant-physiologically tolerated salts thereof, and fungicides containing these compounds.

7 Claims, No Drawings

N,N'-DISUBSTITUTED PIPERAZINES

The present invention relates to novel N,N-disubstituted piperazines, processes for their preparation, their use as fungicides, fungicides which contain the novel active ingredients, and methods for controlling harmful fungi with these active ingredients.

N,N-Alkyl- or aryl-disubstituted piperazine derivatives have been disclosed as pharmacologically active agents and as feed additives (GB 850 662, U.S. Pat. No. 2 943 090, BE-588 826 U.S. Pat. No. 2 927 924, DE-28 09 209, BE 853 899, BE 840 326, DE-22 63 211, DE-20 50 684, BE 756 127, U.S. Pat. No. 4 523 014).

DE 30 28 483 discloses N,N'-dialkylpiperazines of the formula V

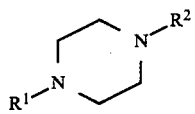

where $R^1$ is $C_1$–$C_{12}$-alkyl, cycloalkyl or hydroxyalkyl and $R^2$ is alkyl-substituted or cycloalkyl-substituted $C_6$–$C_{20}$-aryl, as compounds which prevent bleaching of diazotypes.

DE-2 727 482 discloses the dialkylpiperazine derivative VI as a compound having a fungicidal action.

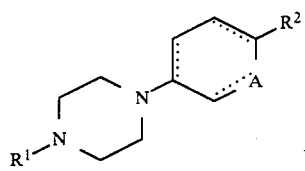

It is an object of the present invention to provide novel compounds of this type having improved properties as fungicides.

We have found that this object is achieved and that N,N'-disubstituted piperazines of the formula I

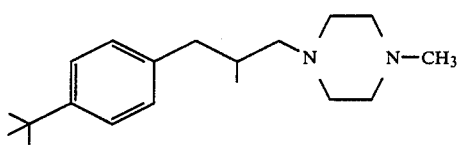

where the group ........ is unsaturated (=) or saturated (—) and A is —, —CH=, —CH$_2$— or —CH$_2$—CH$_2$—, $R^1$ is branched or straight-chain $C_2$–$C_{20}$-alkyl, $C_3$–$C_{20}$-alkenyl, $C_3$–$C_{20}$-alkynyl, $C_4$–$C_{12}$-cycloalkyl, $C_4$–$C_{12}$-cycloalkenyl, $C_4$–$C_{20}$-alkylcycloalkyl, $C_4$–$C_{20}$-cycloalkenylalkyl, $C_4$–$C_{20}$-alkylcycloalkenyl, $C_9$–$C_{11}$-bicycloalkyl, $C_{10}$–$C_{15}$-bicycloalkylalkyl or $C_{10}$–$C_{15}$-alkylbicycloalkyl, and these radicals may be unsubstituted or monosubstituted to trisubstituted by hydroxyl, 1–3 halogen atoms, such as chlorine, bromine or fluorine, $C_1$–$C_5$-alkoxy or $C_3$–$C_9$-trialkylsilyl, $R^1$ may furthermore be 5-membered to 7-membered heterocycloalkyl having 1 or 2 heteroatoms from the group consisting of oxygen and/or sulfur, 5-membered to 7-membered heterocycloalkylmethyl having 1 or 2 heteroatoms from the group consisting of oxygen and/or sulfur, or 5-membered to 7-membered heterocycloalkylmethyl which is monosubstituted to trisubstituted by $C_1$–$C_8$-alkyl and has 1 or 2 heteroatoms from the group consisting of oxygen and/or sulfur, and $R^2$ is branched $C_3$–$C_{10}$-alkyl, branched $C_3$–$C_8$-alkoxy, $C_3$–$C_7$-cycloalkyl, trimethylsilyl or $C_3$–$C_8$-alkylthio, and their salts which are physiologically tolerated by plants are excellent fungicides and well tolerated by plants.

Salts of the piperazines are salts with any inorganic or organic acids, for example with hydrochloric acid, hydrobromic acid, sulfuric acid, phosphoric acid, dodecylbenzenesulfonic acid, formic acid, acetic acid, propionic acid, palmitic acid, perfluoroheptanoic acid, oxalic acid, malonic acid, benzoic acid, malic acid or dodecylsulfonic acid.

The novel [sic] N,N'-disubstituted piperazines of the formula I and their salts which are physiologically tolerated by plants contain chiral centers. They are generally obtained as racemates or may be obtained as diastereomeric mixtures.

In the case of some of the novel compounds, pure diastereomeric compounds can be isolated, for example, by distillation or column chromatography or on the basis of solubility differences. Pure enantiomeric compounds can be obtained, for example, by resolution of racemates with a chiral auxiliary reagent by a known method, for example via diastereomeric salts. Both the diastereomers of the novel N,N'-disubstituted piperazines of the formula I or their salts which are physiologically tolerated by plants and their stereoisomeric mixtures obtained in the synthesis are suitable for use as fungicides. The present invention relates to all these compounds.

Preferred compounds I are those in which A has the abovementioned meanings, so that the group

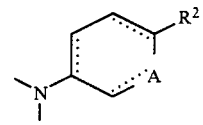

has, for example, the following meanings:

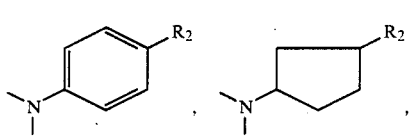

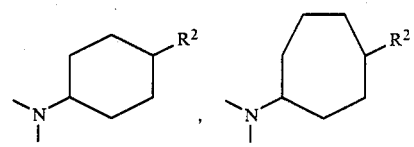

and $R^1$ is $C_2$–$C_{20}$-alkyl, in particular $C_3$–$C_{19}$-alkyl, for example propyl, isopropyl, butyl, isobutyl, but-2-yl, tert-butyl, pentyl, pent-2-yl, pent-3-yl, 1,2-dimethylpropyl, 2,2-dimethylpropyl, hexyl, hex-2-yl, hex-3-yl, 2,3,3-trimethylbut-2-yl, 4-methylpent-2-yl, 4-methylpentyl, 3,3-dimethylbutyl, heptyl, hept-2-yl, hept-3-yl, hept-4-yl, diisopropylmethyl, 1,4-dimethylpentyl, 4,4-dimethylpentyl, octyl, 2-methylhept-3-yl, 5-methylhept-3-yl, oct-2-yl, oct-3-yl, oct-4-yl, 5,5-dimethylhexyl, 2,4,4-trimethylpentyl, 6-methylhept-2-yl, nonyl, non- 2-yl, non-3-yl, non-4-yl, non-5-yl, 2,5,5-trimethylhexyl, 2,6-dimethylhept-4-yl, 3,5,5-trimethylhexyl, decyl, dec-2-yl, dec-3-yl, dec-4-yl, 2,3,5,5-tetramethylhexyl, undecyl, dodecyl, tridecyl, 1,5,9-trimethyldecyl or tetradecyl, $C_2$–$C_{20}$-hydroxyalkyl, in particular $C_2$–$C_8$-hydroxyalkyl, for example hydroxyethyl, hydroxypropyl, hydroxybutyl, hydroxypentyl, hydroxyhexyl, hydroxyheptyl, 1-hydroxybut-2-yl or 2-hydroxybut-3-yl, $C_2$–$C_{20}$-haloalkyl having 1–3 halogen atoms, such as chlorine, bromine or fluorine, in particular $C_2$–$C_{10}$-haloalkyl having 1–3 halogen atoms, such as chlorine, bromine or fluorine, for example 3-chloropropyl, 6-chlorohexyl, trifluoroethyl, trichloroethyl, 5-chloropent-2-yl, 3-chlorobut-2-yl or 3,3-dichloroprop-2-yl, $C_1$–$C_5$-alkoxy-$C_2$–$C_{20}$-alkyl, in particular $C_2$–$C_4$-alkoxy-$C_2$–$C_{10}$-alkyl, for example methoxyethyl, ethoxy-ethyl, tert-butoxyethyl, 3-tert-butoxypropyl, 4-tert-butoxybutyl, methoxypropyl, methoxybutyl, methoxypentyl, methoxyhexyl, ethoxyhexyl or 3-methoxyprop-2-yl, $C_3$–$C_9$-trialkylsilyl-$C_2$–$C_{20}$-alkyl, in particular $C_3$–$C_6$-trialkylsilyl-$C_2$–$C_{10}$-alkyl, for example trimethylsilylethyl, trimethylsilylpropyl, trimethylsilylbutyl, trimethylsilylpentyl or 6-trimethylsilylhexyl, $C_3$–$C_{20}$-alkenyl, in particular $C_3$–$C_{14}$-alkenyl, for example allyl, methallyl, dimethylallyl, hexenyl or 1,5,9-trimethyldecadienyl, $C_3$–$C_{20}$-alkynyl, in particular $C_3$–$C_{14}$-alkynyl, for example propargyl or 4,4-dimethylbut-2-yn-1-yl, $C_4$–$C_{12}$-cycloalkyl, for example cyclobutyl, cyclopentyl, cyclohexyl, cycloheptyl or cyclododecyl, $C_4$–$C_{12}$-hydroxycycloalkyl, for example 4-hydroxycyclohexyl, $C_1$–$C_5$-alkoxy-$C_4$–$C_{12}$-cycloalkyl, such as 4-methoxycyclohexyl or 4-tert-butoxycyclohexyl, $C_3$–$C_9$-trialkylsilyl-$C_4$–$C_{12}$-cycloalkyl, for example 4-trimethylsilylcyclohexyl, $C_4$–$C_{12}$-cycloalkenyl, for example cyclopentenyl, cyclohexenyl or cycloheptenyl, $C_4$–$C_{20}$-alkylcyclohexyl, for example 3,3-dimethylcyclopentyl, 3,3,5-trimethylcyclopentyl, 4-methylcyclohexyl, 3-methylcyclohexyl, 3,3-dimethylcyclohexyl, 3-ethylcyclohexyl, 3,3,5-trimethylcyclohexyl, 4-isopropylcyclohexyl, 3-ethyl-5-methylcyclohexyl, 4-tert-butylcyclohexyl, 4-(2-methylbut-2-yl)-cyclohexyl or 4-(2,4,4-trimethylpent-2-yl)-cyclohexyl, $C_4$–$C_{20}$-alkylhydroxycycloalkyl, for example 4-hydroxy-3,6-dimethylcyclohexyl, 4-hydroxy-3,3-dimethylcyclohexyl or 4-hydroxy-3,3,5-trimethylcyclohexyl, $C_4$–$C_{20}$-cycloalkylalkyl, for example cyclohexylmethyl, cyclohexylethyl or cyclohexylpropyl, $C_4$–$C_{20}$-alkylcycloalkenyl, for example 4-isopropylcyclohexenyl or 4-tert-butylcyclohexenyl, $C_{9-11}$-bicyclo-alkyl, for example bicyclo[4.3.0]nonyl or decalyl, $C_9$–$C_{11}$-hydroxybicycloalkyl, for example 6-hydroxy-2-decalyl or 7-hydroxy-2-decalyl, $C_{10}$–$C_{15}$-alkylbicycloalkyl, for example 9-methyl-2-decalyl, 5,9-dimethyl-2-decalyl or 5,5,9-trimethyl-2-decalyl, $C_{10}$–$C_{15}$-alkylhydroxybicycloalkyl, for example 6-hydroxy-9-methyl-2-decalyl, 6-hydroxy-5,9-dimethyl-2-decalyl or 6-hydroxy-5,5,9-trimethyl-2-decalyl, $C_8$–$C_{10}$-alkoxycycloalkyl, for example 1,4-dioxaspiro[4,5]decan-8-yl, 5-membered to 7-membered heterocycloalkyl having 1 or 2 heteroatoms from the group consisting of oxygen and sulfur, for example tetrahydropyranyl, tetrahydrothiopyranyl or dioxanyl, 5-membered to 7-membered heterocycloalkylmethyl having 1 or 2 heteroatoms from the group consisting of oxygen and sulfur, for example tetrahydropyranylmethyl or dioxanylmethyl, or $C_1$–$C_8$-alkyl-substituted 5-membered to 7-membered heterocycloalkylmethyl having 1 or 2 heteroatoms from the group consisting of oxygen and sulfur, for example 3,5-diethyldioxan-2-ylmethyl, 3,6-diethyldioxan-2-ylmethyl or 3,5-dimethyldioxan-2-ylmethyl, and $R^2$ is branched $C_3$–$C_{10}$-alkyl or branched $C_3$–$C_8$-alkoxy, for example isopropyl, sec-butyl, isobutyl, tert-butyl, 2-methylbut-2-yl, 2,4,4-trimethylpent-2-yl, i-propyl, sec-butoxy or tert-butoxy, $C_3$–$C_7$-cycloalkyl, such as cyclopentyl, cyclohexyl or cycloheptyl, or $C_3$–$C_8$-alkylthio, for example tert-butylthio, sec-butylthio, isobutylthio or n-butylthio.

The compounds of the formula I can be prepared, for example, by N-alkylation of an N-alkylpiperizine of the structure II

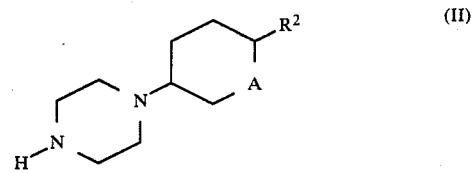

(a) Reaction of a compound II with a compound $R^1$-X under basic conditions

Examples of radicals X are chlorine, bromine, iodine, methanesulfonyl, benzenesulfonyl, p-toluenesulfonyl and the radicals corresponding to the abovementioned anions X.

The reaction is carried out, for example, at 40°–200° C., in the presence or absence of an inert solvent. Preferred bases are inorganic bases, for example potassium hydroxide, sodium hydroxide, lithium hydroxide, sodium hydride, potassium carbonate or sodium carbonate. Organic bases, such as triethylamine, dicyclohexylamine and diisopropylamine, are also suitable. The reaction can also be carried out using an excess of the piperazine derivative II.

(b) Reaction of a carbonyl compound III

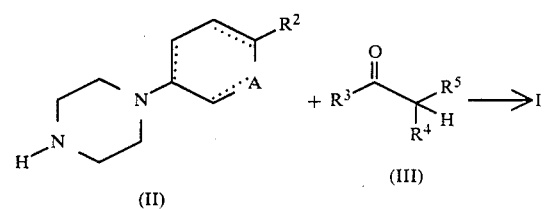

where the radicals $R^3$ to $R^5$ are defined so that the radical IV

in its entirety corresponds to the radical $R^1$, with a piperazine derivative II with simultaneous or subsequent reduction or hydrogenation.

(b₁) In the direct method for the preparation of a compound I, a mixture of II and III is reacted with sodium cyanoborohydride or sodium borohydride in the presence of a solvent, for example methanol, ethanol, propanol or isopropanol, which may contain up to 25% by volume of water, and in the presence or absence of a metal salt, for example zinc(II) chloride, at 0°–100° C., preferably 20°–80° C., or with hydrogen in the presence of a solvent, for example methanol, ethanol, tetrahydrofuran or toluene, and of a hydrogenation catalyst, for example Raney nickel, platinum(IV) oxide, Ru₂O₃ or palladium on carbon, in an autoclave at 100°–150° C. until the pressure remains constant.

in methanol at 20°–60° C. and subsequent alkaline hydrolysis of the N-formyl-N'-cycloalkylpiperazine derivative X.

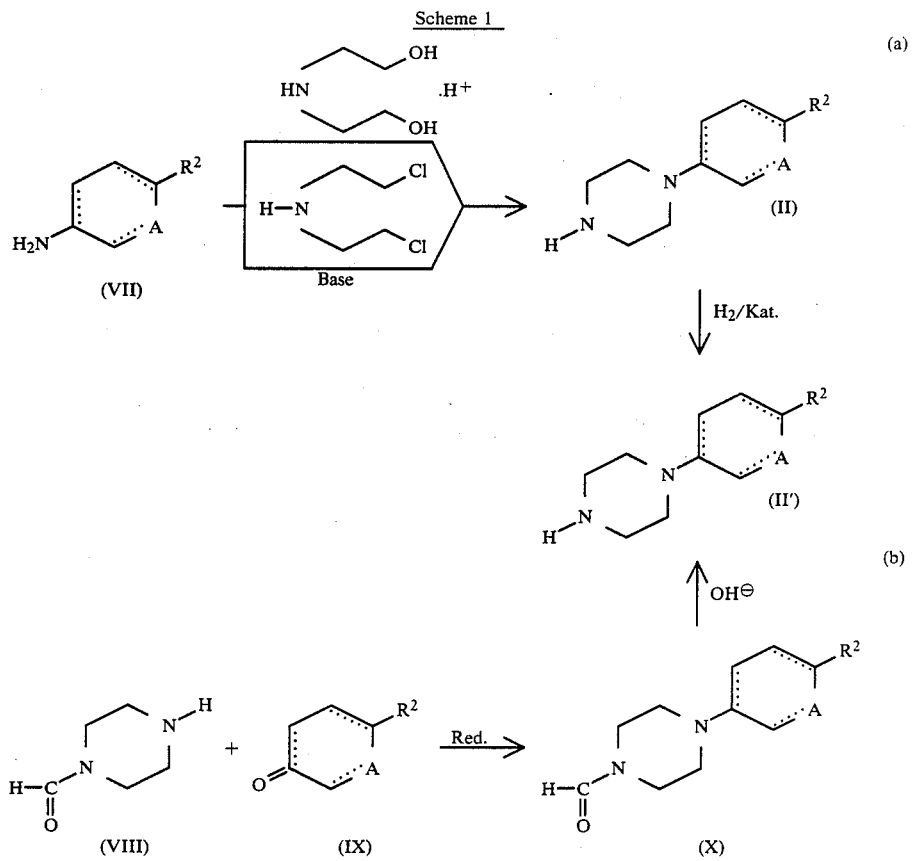

Scheme 1

(b₂) In the two-stage reaction, an enamine is prepared from the compounds II and III under dehydrating conditions, and the said enamine is then reduced using a noble metal catalyst, such as Raney nickel, Raney cobalt, PtO₂ or Ru₂O₃, preferably palladium on carbon, and hydrogen.

The N-monosubstituted piperazines II used as starting compounds can be prepared by reactions which synthesize the piperazine ring (cf. for example PRATT, Y.T.: The Pyrazines and Piperazines, in: R. C. ELDERFIELD (Editor): Heterocyclic Compounds, Vol. 6, New York-London, 1957) or by derivatization of pyrazine derivatives. Possible syntheses are shown in scheme 1.

(a) For example, a substituted amine VII can be reacted with diethanolamine with acid catalysis (HCl, HBr or H₂SO₄) at 200°–250° C. or with N,N-bischloroethylamine in an organic solvent, for example diethyleneglycol dimethyl ether, ethanol, acetone, acetone/water or dimethylformamide, in the presence of an auxiliary base, such as potassium carbonate or sodium carbonate, at 60°–250° C. to give II.

Where the compound VII is an aniline, the N-cyclohexylpiperazine derivative II' can be obtained from the resulting N-phenylpiperazine derivative II by catalytic hydrogenation.

(b) The cycloaliphatically N-substituted piperazines II' can also be obtained via reductive amination of N-formylpiperazine VIII with a correspondingly substituted cycloalkanone IX and a suitable reducing agent, for example sodium cyanoborohydride/zinc chloride, The Examples below illustrate the preparation of the novel compounds.

PREPARATION EXAMPLES

Method 1

Preparation of the starting compound N-(4-tert-butylphenyl)-piperazine 149 g (1 mole) of 4-tert-butylaniline, 178.5 g (1 mole) of bis-(2-chloroethylamine) hydrochloride and 138 g (1 mole) of potassium carbonate in 600 ml of diethylene glycol dimethyl ether are refluxed for 90 hours. The mixture is rendered strongly alkaline with 1 l of water and concentrated sodium hydroxide solution and stirred for 2 hours. The organic phase is extracted with 3×250 ml of methyl tert-butyl ether and the combined organic phases are washed with 2×250 ml of water, dried over sodium sulfate and evaporated down under reduced pressure. The residue is fractionated under reduced pressure to give 155 g (71% of theory) of a product of boiling point 114°–117° C./0.01 mbar and melting point 48°–52° C.

Method 2

Preparation of the starting compound N-(4-Tert-butylcyclohexyl)-piperazine 90 g (0.41 mole) of N-(4-tert-butylphenyl)-piperazine in 1.6 l of dioxane are hydrogenated over 5 g of ruthenium(IV) oxide at 130° C. and under 150 bar for 74 hours. Working up in the usual manner gives a white solid.

EXAMPLE 1

N-(3,3-dimethylcyclohexyl)-N'-(4-tert-butylcyclohexyl)-piperazine (Compound No. 162)

5.0 g (22.3 millimoles) of N-(4-tert-butylcyclohexyl)-piperazine, 5.4 g (44.6 millimoles) of 3,3-dimethylcyclohexanone, 1.7 g (12.3 millimoles) of zinc(II) chloride and 1.6 g (24.5 millimoles) of sodium cyanoborohydride are stirred for 48 hours at 20° C. The mixture is evaporated down under reduced pressure, the residue is hydrolyzed with 1N sodium hydroxide solution and the mixture is extracted with methyl tert-butyl ether. Working up the organic extract in the usual manner gives 3.7 g (50% of theory) of a product in the form of white crystals (mp. 90°–92° C.; for IR data, see Table 1b).

EXAMPLE 2

N-(4-Tert-butylphenyl-N'-(3,3-dimethylbutyl)-piperazine (Compound No. 17)

5 g (22.9 millimoles) of N-(4-tert-butylphenyl)-piperazine, 8.3 g (68.7 millimoles) of neohexyl chloride, 3.2 g (22.9 millimoles) of potassium carbonate and 3.8 g (22.9 millimoles) of potassium iodide are stirred for 16 hours at 140° C. The mixture is taken up in dichloromethane and dilute sodium hydroxide solution. The organic phase is washed, dried over sodium sulfate and evaporated down under reduced pressure, and the residue is chromatographed over silica gel using 1:1 methyl tert-butyl ether/hexane to give 1.5 g (22% of theory) of a colourless oil (for IR data, see Table 1a).

The novel compounds listed in Tables 1a/b can be prepared similarly to Examples 1 and 2.

TABLE 1a

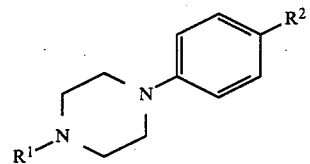

| Comp. no. | R¹ | R² | B.p. (°C./mbar) M.p. (°C.) | IR absorption (cm⁻¹) [Film] |
|---|---|---|---|---|
| 1 | n-propyl | tert.-butyl | | |
| 2 | isopropyl | tert.-butyl | | |
| 3 | n-butyl | tert.-butyl | 41–45 | 2957, 2925, 2871, 2823, 1517, 1239, 1227, 819 |
| 4 | isobutyl | tert.-butyl | 35–36 | 2954, 2926, 2869, 2816, 1518, 1454, 1232, 821 |
| 3 | sec.-butyl | tert.-butyl | | |
| 4 | tert.-butyl | tert.-butyl | | |
| 5 | n-pentyl | tert.-butyl | | |
| 6 | 3-methyl-butyl | tert.-butyl | 145/0,2 | 2955, 2870, 2817, 1518, 1466, 1456, 1363, 1230 |
| 7 | 2,2-dimethyl-propyl | tert.-butyl | | |
| 8 | pent-2-yl | tert.-butyl | | |
| 9 | pent-3-yl | tert.-butyl | | |
| 10 | 1,2-dimethyl-propyl | tert.-butyl | | |
| 11 | n-hexyl | tert.-butyl | | |
| 12 | hex-2-yl | tert.-butyl | | |
| 13 | Hex-3-yl | tert.-butyl | | |
| 14 | 1,2,2-trimethyl-propyl | tert.-butyl | | |
| 15 | 1,3-dimethylbutyl | tert.-butyl | | |
| 16 | 4-methyl-pentyl | tert.-butyl | | |
| 17 | 3,3-dimethyl-butyl | tert.-butyl | oil | 2953, 2866, 2818, 1611, 1519, 1456, 1364, 1236, 1131, 820 |
| 18 | n-heptyl | tert.-butyl | | |
| 19 | hept-2-yl | tert.-butyl | | |
| 20 | hept-3-yl | tert.-butyl | | |
| 21 | hept-4-yl | tert.-butyl | | |
| 22 | diisopropyl-methyl | tert.-butyl | | |
| 23 | 1,4-dimethyl-pentyl | tert.-butyl | | |
| 24 | 4,4-dimethyl-pentyl | tert.-butyl | 65 | 2955, 2903, 2867, 1517, 1468, 1365, 1236, 824 |
| 25 | 3,3-dimethyl-2-hydroxybutyl | tert.-butyl | 137–138 | 2964, 2949, 2833, 1520, 1365, 1333, 1272, 819 |
| 26 | n-octyl | tert.-butyl | | |
| 27 | 2-methyl-hept-3-yl | tert.-butyl | | |
| 28 | 5-methyl-hept-3-yl | tert.-butyl | | |
| 29 | oct-2-yl | tert.-butyl | | |
| 30 | oct-3-yl | tert.-butyl | | |
| 31 | oct-4-yl | tert.-butyl | | |
| 32 | 5,5-dimethyl-hexyl | tert.-butyl | | |
| 33 | 2,4,4-trimethyl-pentyl | tert.-butyl | oil | 2958, 2899, 2866, 2828, 2810, 1516, 1374, 1237 |
| 34 | 6-methyl-hept-2-yl | tert.-butyl | | |
| 35 | n-nonyl | tert.-butyl | | |
| 36 | non-2-yl | tert.-butyl | | |
| 37 | non-3-yl | tert.-butyl | | |
| 38 | non-4-yl | tert.-butyl | | |
| 39 | non-5-yl | tert.-butyl | | |
| 40 | 2,5,5-trimethyl-hexyl | tert.-butyl | | |
| 41 | 2,6-dimethyl-hept-4-yl | tert.-butyl | | |
| 42 | 3,5,5-trimethyl-hexyl | tert.-butyl | oil | 2955, 2905, 2868, 2817, 1519, 1465, 1457, 1364, 1231 |
| 43 | n-decyl | tert.-butyl | | |
| 44 | dec-2-yl | tert.-butyl | | |

TABLE 1a-continued

| Comp. no. | R¹ | R² | B.p. (°C./mbar) M.p. (°C.) | IR absorption (cm⁻¹) [Film] |
|---|---|---|---|---|
| 45 | dec-3-yl | tert.-butyl | | |
| 46 | dec-4-yl | tert.-butyl | | |
| 47 | 2,3,5,5-Tetramethylhexyl | tert.-butyl | | |
| 48 | n-undecyl | tert.-butyl | | |
| 49 | n-dodecyl | tert.-butyl | | |
| 50 | n-tridecyl | tert.-butyl | | |
| 51 | 1,5,9-trimethyl-decyl | tert.-butyl | | |
| 52 | n-tetradecyl | tert.-butyl | | |
| 53 | 2-hydroxyethyl | tert.-butyl | | |
| 54 | 3-hydroxypropyl | tert.-butyl | | |
| 55 | 4-hydroxy-butyl | tert.-butyl | | |
| 56 | 1-hydroxy-but-2-yl | tert.-butyl | | |
| 57 | 2-hydroxy-but-3-yl | tert.-butyl | | |
| 58 | 3-chloropropyl | tert.-butyl | | |
| 59 | 6-chlorohexyl | tert.-butyl | | |
| 60 | 3-chloro-2-butenyl | tert.-butyl | 61 | 2957, 2869, 2811, 1517, 1453, 1364, 1231, 1148, 1004, 824 |
| 61 | trichloroethyl | tert.-butyl | | |
| 62 | 5-chloro-pent-1-yl | tert.-butyl | | |
| 63 | 3-chloro-but-2-yl | tert.-butyl | | |
| 64 | 3,3-dichloro-prop-2-yl | tert.-butyl | | |
| 65 | 2-methoxyethyl | tert.-butyl | | |
| 66 | 2-ethoxyethyl | tert.-butyl | | |
| 67 | 2-tert.-butoxyethyl | tert.-butyl | | |
| 68 | 3-tert.-butoxy-propyl | tert.-butyl | | |
| 69 | 6-methoxyhexyl | tert.-butyl | | |
| 70 | 3-methoxy-prop-2-yl | tert.-butyl | | |
| 71 | trimethylsilylethyl | tert.-butyl | | |
| 72 | 3-trimethylsilyl-propyl | tert.-butyl | | |
| 73 | 6-trimethylsilyl-hexyl | tert.-butyl | | |
| 74 | allyl | tert.-butyl | | |
| 75 | 3-methyl-but-2-en-yl | tert.-butyl | | |
| 76 | 1,5,9-trimethyl-deca-4,8-dienyl | tert.-butyl | | |
| 77 | propargyl | tert.-butyl | | |
| 78 | 4,4-dimethyl-but-in-1-yl | tert.-butyl | | |
| 79 | cyclopentyl | tert.-butyl | | |
| 80 | 3-methyl-cyclopentyl | tert.-butyl | | |
| 81 | 3,3-dimethyl-cyclopentyl | tert.-butyl | | |
| 82 | 3,3,5-trimethyl-cyclopentyl | tert.-butyl | | |
| 83 | cyclohexyl | | oil | 2967, 2948, 2924, 2853, 2828, 1518, 1231 813 |
| 84 | 3-methyl-cyclohexyl | | | |
| 85 | 3,3-dimethyl-cyclohexyl | tert.-butyl | 175/0,2 | 2951, 2931, 2862, 2811, 1519, 1450, 1235 820 |
| 86 | 3-ethyl-cyclohexyl | tert.-butyl | | |
| 87 | 3-ethyl-5-methyl-cyclohexyl | tert.-butyl | 80–82 | 2960, 2923, 2864, 1520, 1461, 1449, 1236 1228 |
| 88 | 4-methyl-cyclohexyl | tert.-butyl | | |
| 89 | cycloheptyl | tert.-butyl | | |
| 90 | 4-isopropyl-cyclohexyl (isomer mixture) | tert.-butyl | | |
| 91 | 3,3,5-trimethyl-cyclohexyl | tert.-butyl | oil | 2949, 2905, 2865, 2820, 1518, 1452, 1232, 823 |
| 92 | 3,3,5,5-tetramethylcyclohexyl | tert.-butyl | 133 | 2952, 2922, 2900, 2822, 2813, 1519, 1234, 820 |
| 93 | 4-hydroxy-cyclohexyl | tert.-butyl | | |
| 94 | 4-tert.-butoxy-cyclohexyl | tert.-butyl | | |
| 95 | cyclohex-2-en-yl | tert.-butyl | | |
| 96 | 4-tert.-butyl-cyclohexyl (isomer mixture) | tert.-butyl | 128–30 | 2963, 2939, 2866, 2813, 1521, 1446, 1366, 1246, 1232 |
| 97 | trans-4-tert.-butyl-cyclohexyl | tert.-butyl | | |
| 98 | 4(2-methyl-but-2-yl)cyclohexyl (isomer mixture) | tert.-butyl | | |
| 99 | trans-4(2-methyl-but-2-yl)-cyclohexyl | tert.-butyl | | |
| 100 | 4(2,4,4-trimethyl-pent-2-yl) cyclohexyl (isomer mixture) | tert.-butyl | | |
| 101 | trans-4(2,4,4-trimethyl-pent-2-yl)cyclohexyl | tert.-butyl | | |
| 102 | 4-hydroxy-3-methyl-cyclohexyl | tert.-butyl | | |
| 103 | 4-hydroxy-3,6-dimethyl-cyclohexyl | tert.-butyl | | |

TABLE 1a-continued

[Structure: piperazine with R¹ on one N and 4-R²-phenyl on the other N]

| Comp. no. | R¹ | R² | B.p. (°C/mbar) M.p. (°C) | IR absorption (cm$^{-1}$) [Film] |
|---|---|---|---|---|
| 104 | 4-hydroxy-3,3-dimethyl-cyclohexyl | tert.-butyl | | |
| 105 | 4-hydroxy-3,3,5-trimethyl-cyclohexyl | tert.-butyl | | |
| 106 | cyclohexylmethyl | tert.-butyl | | |
| 107 | cyclohexylethyl | tert.-butyl | 75–77 | 2946, 2920, 2851, 2818, 1517, 1447, 1234, 830 |
| 108 | 4-tert.-butyl-cyclohex-3-en-yl | tert.-butyl | | |
| 109 | 4-tert.-butyl-cyclohex-2-en-yl | tert.-butyl | | |
| 110 | 1-decalyl (cis/trans mixture) | tert.-butyl | | |
| 111 | 2-decalyl (cis/trans mixture) | tert.-butyl | 80 | 2961, 2922, 2854, 2825, 1612, 1518, 1447, 1364<br>1234, 8177 |
| 112 | trans-2-decalyl (eq/ax.-substituted) | tert.-butyl | | |
| 113 | eq.-trans-2-decalyl | tert.-butyl | | |
| 114 | 6-hydroxy-2-decalyl | tert.-butyl | | |
| 115 | 7-hydroxy-2-decalyl | tert.-butyl | | |
| 116 | 2-decalymethyl | tert.-butyl | | |
| 117 | 9-methyl-trans-2-decalyl | tert.-butyl | | |
| 118 | 5,9-dimethyl-trans-2-decalyl | tert.-butyl | | |
| 119 | 5,5,9-trimethyl-trans-2-decalyl | tert.-butyl | | |
| 120 | 6-hydroxy-9-methyl-2-decalyl | tert.-butyl | | |
| 121 | 6-hydroxy-5,9-dimethyl-2-decalyl | tert.-butyl | | |
| 122 | 6-hydroxy-5,5,9-trimethyl-2-decalyl | tert.-butyl | | |
| 123 | tetrahydropyran-4-yl | tert.-butyl | | |
| 124 | tetrahydrothiopyran-4-yl | tert.-butyl | | |
| 125 | dioxan-2-yl-methyl | tert.-butyl | | |
| 126 | tetrahydropyran-2-yl-methyl | tert.-butyl | | |
| 127 | tetrahydropyran-3-yl-methyl | tert.-butyl | | |
| 128 | 3,5-dimethyl-dioxan-2-yl-methyl | tert.-butyl | | |
| 129 | 3,5-diethyl-dioxan-2-yl-methyl | tert.-butyl | | |
| 130 | 3,6-diethyl-dioxan-2-yl-methyl | tert.-butyl | | |
| 131 | 1,4-dioxa-spiro[4,5]decan-8-yl | tert.-butyl | oil | 2958, 2882, 1519, 1250, 1234, 1148, 1129 |

[Structure: 4-methylcyclohexyl group with 1,3-dioxolane substituent]

| Comp. no. | R¹ | R² | B.p. (°C/mbar) M.p. (°C) | IR absorption (cm$^{-1}$) [Film] |
|---|---|---|---|---|
| 132 | 4-trimethylsilyl-cyclohexyl | tert.-butyl | | |
| 133 | n-propyl | 1,1-dimethyl-propyl | | |
| 134 | isopropyl | 1,1-dimethyl-propyl | | |
| 135 | n-butyl | 1,1-dimethyl-propyl | | |
| 136 | isobutyl | 1,1-dimethyl-propyl | | |
| 137 | sec.-butyl | 1,1-dimethyl-propyl | | |
| 138 | tert.-butyl | 1,1-dimethyl-propyl | | |
| 139 | n-pentyl | 1,1-dimethyl-propyl | | |
| 140 | 3-methyl-butyl | 1,1-dimethyl-propyl | | |
| 141 | 2,2-dimethyl-propyl | 1,1-dimethyl-propyl | | |
| 142 | pent-2-yl | 1,1-dimethyl-propyl | | |
| 143 | pent-3-yl | 1,1-dimethyl-propyl | | |
| 144 | 1,2-dimethyl-propyl | 1,1-dimethyl-propyl | | |
| 145 | n-hexyl | 1,1-dimethyl-propyl | | |
| 146 | hex-2-yl | 1,1-dimethyl-propyl | | |
| 147 | hex-3-yl | 1,1-dimethyl-propyl | | |
| 148 | 1,2,2-trimethyl-propyl | 1,1-dimethyl-propyl | | |
| 149 | 1,3-dimethylbutyl | 1,1-dimethyl-propyl | | 2959, 2876, 2818, 1518, 1465, 1450, 1364<br>1231 |
| 150 | 4-methyl-pentyl | 1,1-dimethyl-propyl | | |
| 151 | 3,3-dimethyl-butyl | 1,1-dimethyl-propyl | resin | |
| 152 | n-heptyl | 1,1-dimethyl-propyl | | |
| 153 | hept-2-yl | 1,1-dimethyl-propyl | | |
| 154 | hept-3-yl | 1,1-dimethyl-propyl | | |
| 155 | hept-4-yl | 1,1-dimethyl-propyl | | |
| 156 | diisopropyl-methyl | 1,1-dimethyl-propyl | | |
| 157 | 1,4-dimethyl-pentyl | 1,1-dimethyl-propyl | | |

TABLE 1a-continued

[Structure: piperazine with R¹-N and N-phenyl-R² substituents]

| Comp. no. | R¹ | R² | B.p. (°C./mbar) M.p. (°C.) | IR absorption (cm$^{-1}$) [Film] |
|---|---|---|---|---|
| 158 | 4,4-dimethyl-pentyl | 1,1-dimethyl-propyl | oil | 2955, 2877, 2817, 1518, 2475, 1466, 1364, 1247, 1229 |
| 159 | 3,3-dimethyl-2-hydroxy-butyl | 1,1-dimethyl-propyl | | |
| 160 | n-octyl | 1,1-dimethyl-propyl | | |
| 161 | 2-methyl-hept-3-yl | 1,1-dimethyl-propyl | | |
| 162 | 5-methyl-hept-3-yl | 1,1-dimethyl-propyl | | |
| 163 | oct-2-yl | 1,1-dimethyl-propyl | | |
| 164 | oct-3-yl | 1,1-dimethyl-propyl | | |
| 165 | oct-4-yl | 1,1-dimethyl-propyl | | |
| 166 | 5,5-dimethyl-hexyl | 1,1-dimethyl-propyl | | |
| 167 | 2,4,4-trimethyl-pentyl | 1,1-dimethyl-propyl | oil | 2959, 2914, 2877, 2816, 1518, 1464, 1455, 1229 |
| 168 | 6-methyl-hept-2-yl | 1,1-dimethyl-propyl | | |
| 169 | n-nonyl | 1,1-dimethyl-propyl | | |
| 170 | non-2-yl | 1,1-dimethyl-propyl | | |
| 171 | non-3-yl | 1,1-dimethyl-propyl | | |
| 172 | non-4-yl | 1,1-dimethyl-propyl | | |
| 173 | non-5-yl | 1,1-dimethyl-propyl | | |
| 174 | 2,5,5-trimethyl-hexyl | 1,1-dimethyl-propyl | | |
| 175 | 2,6-dimethyl-hept-4-yl | 1,1-dimethyl-propyl | | |
| 176 | 3,5,5-trimethyl-hexyl | 1,1-dimethyl-propyl | | |
| 177 | n-decyl | 1,1-dimethyl-propyl | | |
| 178 | dec-2-yl | 1,1-dimethyl-propyl | | |
| 179 | dec-3-yl | 1,1-dimethyl-propyl | | |
| 180 | dec-4-yl | 1,1-dimethyl-propyl | | |
| 181 | 2,3,5,5-tetramethylhexyl | 1,1-dimethyl-propyl | | |
| 182 | n-undecyl | 1,1-dimethyl-propyl | | |
| 183 | n-dodecyl | 1,1-dimethyl-propyl | | |
| 184 | n-tridecyl | 1,1-dimethyl-propyl | | |
| 185 | 1,5,9-trimethyl-decyl | 1,1-dimethyl-propyl | | |
| 186 | n-tetradecyl | 1,1-dimethyl-propyl | | |
| 187 | 2-hydroxyethyl | 1,1-dimethyl-propyl | | |
| 188 | 3-hydroxyethyl | 1,1-dimethyl-propyl | | |
| 189 | 4-hydroxy-butyl | 1,1-dimethyl-propyl | | |
| 190 | 1-hydroxy-but-2-yl | 1,1-dimethyl-propyl | | |
| 191 | 2-hydroxy-but-3-yl | 1,1-dimethyl-propyl | | |
| 192 | 3-chloropropyl | 1,1-dimethyl-propyl | | |
| 193 | 6-chlorohexyl | 1,1-dimethyl-propyl | | |
| 194 | 3-chloro-2-butenyl | 1,1-dimethyl-propyl | | |
| 195 | trichloroethyl | 1,1-dimethyl-propyl | | |
| 196 | 5-chloro-pent-2-yl | 1,1-dimethyl-propyl | | |
| 197 | 3-chloro-but-2-yl | 1,1-dimethyl-propyl | | |
| 198 | 3,3-dichloro-prop-2-yl | 1,1-dimethyl-propyl | | |
| 199 | 2-methoxyethyl | 1,1-dimethyl-propyl | | |
| 200 | 2-ethoxyethyl | 1,1-dimethyl-propyl | | |
| 201 | 2-tert.-butoxyethyl | 1,1-dimethyl-propyl | | |
| 202 | 3-tert.-butoxy-ethyl | 1,1-dimethyl-propyl | | |
| 203 | 6-methoxyhexyl | 1,1-dimethyl-propyl | | |
| 204 | 3-methoxy-prop-2-yl | 1,1-dimethyl-propyl | | |
| 205 | trimethylsilylethyl | 1,1-dimethyl-propyl | | |
| 206 | 3-trimethylsilyl-propyl | 1,1-dimethyl-propyl | | |
| 207 | 6-trimethylsilyl-hexyl | 1,1-dimethyl-propyl | | |
| 208 | allyl | 1,1-dimethyl-propyl | | |
| 209 | 3-methyl-but-2-en-yl | 1,1-dimethyl-propyl | | |
| 210 | 1,5,9-trimethyl-deca-4,8-dienyl | 1,1-dimethyl-propyl | | |
| 211 | propargyl | 1,1-dimethyl-propyl | | |
| 212 | 4,4-dimethyl-but-in-1-yl | 1,1-dimethyl-propyl | | |
| 213 | cyclopentyl | 1,1-dimethyl-propyl | | |
| 214 | 3-methyl-cyclopentyl | 1,1-dimethyl-propyl | | |
| 215 | 3,3-dimethyl-cyclopentyl | 1,1-dimethyl-propyl | | |
| 216 | 3,3,5-trimethyl-cyclopentyl | 1,1-dimethyl-propyl | | |
| 217 | cyclohexyl | 1,1-dimethyl-propyl | 48 | 2966, 2926, 2855, 2829, 1519, 1451, 1248, 1228, 813 |
| 218 | 3-methyl-cyclohexyl | 1,1-dimethyl-propyl | | |
| 219 | 3,3-dimethyl-cyclohexyl | 1,1-dimethyl-propyl | oil | 2951, 2930, 2863, 2811, 1519, 1463, 1951, 1364, 1235, 819 |
| 220 | 3,3,5-trimethyl-cyclohexyl | 1,1-dimethyl-propyl | | |
| 221 | 3,3,5,5-tetramethyl-cyclohexyl | 1,1-dimethyl-propyl | | |
| 222 | 3-ethyl-cyclohexyl | 1,1-dimethyl-propyl | | |

TABLE 1a-continued

| Comp. no. | R¹ | R² | B.p. (°C./mbar) M.p. (°C.) | IR absorption (cm⁻¹) [Film] |
|---|---|---|---|---|
| 223 | 3-ethyl-5-methyl-cyclohexyl | 1,1-dimethyl-propyl | | |
| 224 | 4-methyl-cyclohexyl | 1,1-dimethyl-propyl | | |
| 225 | 4-isopropyl-cyclohexyl | 1,1-dimethyl-propyl | | |
| 226 | cycloheptyl | 1,1-dimethyl-propyl | | |
| 227 | 4-hydroxy-cyclohexyl | 1,1-dimethyl-propyl | | |
| 228 | 4-tert.-butoxy-cyclohexyl | 1,1-dimethyl-propyl | | |
| 229 | 4-trimetylsolyl-cyclohexyl (cis/trans mixture) | 1,1-dimethyl-propyl | | |
| 230 | cyclohex-2-en-yl | 1,1-dimethyl-propyl | | |
| 231 | 4-tert.-butyl-cyclohexyl (isomer mixture) | 1,1-dimethyl-propyl | 115 | 2964, 2940, 2865, 2818, 1520, 1447, 1366, 1248, 1228, 813 |
| 232 | trans-4-tert.-butyl-cyclo-hexyl | 1,1-dimethyl-propyl | | |
| 233 | 4(2-methyl-but-2-yl)cyclo-hexyl (isomer mixture) | 1,1-dimethyl-propyl | | |
| 234 | trans-4(2-methyl-but-2-yl)-cyclohexyl | 1,1-dimethyl-propyl | | |
| 235 | 4(2,4,4-trimethyl-pent-2-yl)-cyclohexyl (isomer mixture) | 1,1-dimethyl-propyl | | |
| 236 | trans-4(2,4,4-trimethyl-pent-2-yl)cyclohexyl | 1,1-dimethyl-propyl | | |
| 237 | 4-hydroxy-3-methyl-cyclohexyl | 1,1-dimethyl-propyl | | |
| 238 | 4-hydroxy-3,6-dimethyl-cyclo-hexyl | 1,1-dimethyl-propyl | | |
| 239 | 4-hydroxy-3,3-dimethyl-cyclo-hexyl | 1,1-dimethyl-propyl | | |
| 240 | 4-hydroxy-3,3,5-trimethyl-cyclohexyl | 1,1-dimethyl-propyl | | |
| 241 | cyclohexylmethyl | 1,1-dimethyl-propyl | | |
| 242 | cyclohexylethyl | 1,1-dimethyl-propyl | | |
| 243 | 4-tert.-butyl-cyclohex-3-en-yl | 1,1-dimethyl-propyl | | |
| 244 | 4-tert.-butyl-cyclohex-2-en-yl | 1,1-dimethyl-propyl | | |
| 245 | 1-decalyl (cis/trans mixture) | 1,1-dimethyl-propyl | | |
| 246 | 2-decalyl (cis/trans mixture) | 1,1-dimethyl-propyl | | |
| 247 | trans-2-decalyl (eq/ax.-substituted) | 1,1-dimethyl-propyl | | |
| 248 | eq.-trans-2-decalyl | 1,1-dimethyl-propyl | | |
| 249 | 6-hydroxy-2-decalyl | 1,1-dimethyl-propyl | | |
| 250 | 7-hydroxy-2-decalyl | 1,1-dimethyl-propyl | | |
| 251 | 2-decalylmethyl | 1,1-dimethyl-propyl | | |
| 252 | 9-methyl-trans-2-decalyl | 1,1-dimethyl-propyl | | |
| 253 | 5,9-dimethyl-trans-2-decalyl | 1,1-dimethyl-propyl | | |
| 254 | 5,5,9-trimethyl-trans-2-decalyl | 1,1-dimethyl-propyl | | |
| 255 | 6-hydroxy-9-methyl-2-decalyl | 1,1-dimethyl-propyl | | |
| 256 | 6-hydroxy-5,9-dimethyl-2-decalyl | 1,1-dimethyl-propyl | | |
| 257 | 6-hydroxy-5,5,9-trimethyl-2-decalyl | 1,1-dimethyl-propyl | | |
| 258 | tetrahydropyran-4-yl | 1,1-dimethyl-propyl | | |
| 259 | tetrahydrothiopyran-4-yl | 1,1-dimethyl-propyl | | |
| 260 | dioxan-2-yl-methyl | 1,1-dimethyl-propyl | | |
| 261 | tetrahydropyran-2-yl-methyl | 1,1-dimethyl-propyl | | |
| 262 | tetrahydropyran-3-yl-methyl | 1,1-dimethyl-propyl | | |
| 263 | 3,5-dimethyl-dioxan-2-yl-methyl | 1,1-dimethyl-propyl | | |
| 264 | 3,5-diethyl-dioxan-2-yl-methyl | 1,1-dimethyl-propyl | | |
| 265 | 3,6-diethyl-dioxan-2-yl-methyl | 1,1-dimethyl-propyl | | |
| 266 | | | | |
| 267 | 1,4-dioxa-spiro[4,5-decan]-8-yl | 1,1-dimethyl-propyl | | |
| 268 | n-propyl | sec.-butyl | | |
| 269 | isopropyl | sec.-butyl | | |
| 270 | n-butyl | sec.-butyl | | |
| 271 | isobutyl | sec.-butyl | | |
| 272 | sec.-butyl | sec.-butyl | | |
| 273 | tert.-butyl | sec.-butyl | | |
| 274 | n-pentyl | sec.-butyl | | |
| 275 | 3-methyl-butyl | sec.-butyl | | |
| 276 | 2,2-dimethyl-propyl | sec.-butyl | | |
| 277 | pent-2-yl | sec.-butyl | | |
| 278 | pent-3-yl | sec.-butyl | | |
| 279 | 1,2-dimethyl-propyl | sec.-butyl | | |
| 280 | n-hexyl | sec.-butyl | | |
| 281 | hex-2-yl | sec.-butyl | | |

TABLE 1a-continued

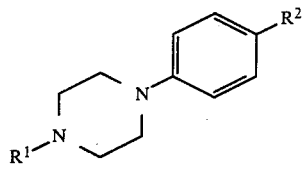

| Comp. no. | R¹ | R² | B.p. (°C./mbar) M.p. (°C.) | IR absorption (cm⁻¹) [Film] |
|---|---|---|---|---|
| 282 | hex-3-yl | sec.-butyl | | |
| 283 | 1,2,2-trimethyl-propyl | sec.-butyl | | |
| 284 | 1,3-dimethyl-butyl | sec.-butyl | | |
| 285 | 4-methyl-pentyl | sec.-butyl | | |
| 286 | 3,3-dimethyl-butyl | sec.-butyl | 50 | 2959, 2871, 2820, 1612, 1516, 1456, 1234, 822 |
| 287 | n-heptyl | sec.-butyl | | |
| 288 | hept-2-yl | sec.-butyl | | |
| 289 | hept-3-yl | sec.-butyl | | |
| 290 | hept-4-yl | sec.-butyl | | |
| 291 | diisopropyl-methyl | sec.-butyl | | |
| 292 | 1,4-dimethyl-pentyl | sec.-butyl | | |
| 293 | 4,4-dimethyl-pentyl | sec.-butyl | oil | 2955, 2872, 2816, 1516, 1454, 1377, 1346, 1246, 1232, 823 |
| 294 | 3,3-dimethyl-2-hydroxy-butyl | sec.-butyl | | |
| 295 | n-octyl | sec.-butyl | | |
| 296 | 2-methyl-hept-3-yl | sec.-butyl | | |
| 297 | 5-methyl-hept-3-yl | sec.-butyl | | |
| 298 | oct-2-yl | sec.-butyl | | |
| 299 | oct-3-yl | sec.-butyl | | |
| 300 | oct-4-yl | sec.-butyl | | |
| 301 | 5,5-dimethyl-hexyl | sec.-butyl | | |
| 302 | 2,4,4-trimethyl-pentyl | sec.-butyl | | |
| 303 | 6-methyl-hept-2-yl | sec.-butyl | | |
| 304 | n-nonyl | sec.-butyl | | |
| 305 | non-2-yl | sec.-butyl | | |
| 306 | non-3-yl | sec.-butyl | | |
| 307 | non-4-yl | sec.-butyl | | |
| 308 | non-5-yl | sec.-butyl | | |
| 309 | 2,5,5-trimethyl | sec.-butyl | | |
| 310 | 2,6-dimethyl-hept-4-yl | sec.-butyl | | |
| 311 | 3,5,5-trimethyl-hexyl | sec.-butyl | | |
| 312 | n-decyl | sec.-butyl | | |
| 313 | dec-2-yl | sec.-butyl | | |
| 314 | dec-3-yl | sec.-butyl | | |
| 315 | dec-4-yl | sec.-butyl | | |
| 316 | 2,3,5,5-tetramethyl-hexyl | sec.-butyl | | |
| 317 | n-undecyl | sec.-butyl | | |
| 318 | n-dodecyl | sec.-butyl | | |
| 319 | n-tridecyl | sec.-butyl | | |
| 320 | 1,5,9-trimethyl-decyl | sec.-butyl | | |
| 321 | n-tetradecyl | sec.-butyl | | |
| 322 | 2-hydroxyethyl | sec.-butyl | | |
| 323 | 3-hydroxypropyl | sec.-butyl | | |
| 324 | 4-hydroxy-butyl | sec.-butyl | | |
| 325 | 1-hydroxy-but-2-yl | sec.-butyl | | |
| 326 | 2-hydroxy-but-3-yl | sec.-butyl | | |
| 327 | 3-chloropropyl | sec.-butyl | | |
| 328 | 6-chlorohexyl | sec.-butyl | | |
| 329 | 5-chloro-pent-2-yl | sec.-butyl | | |
| 330 | 3-chloro-but-2-yl | sec.-butyl | | |
| 331 | 3,3-dichloro-prop-2-yl | sec.-butyl | | |
| 332 | 2-methoxyethyl | sec.-butyl | | |
| 333 | 2-ethoxyethyl | sec.-butyl | | |
| 334 | 2-tert.-butoxyethyl | sec.-butyl | | |
| 335 | 3-tert.-butoxy-ethyl | sec.-butyl | | |
| 336 | 6-methoxyhexyl | sec.-butyl | | |
| 337 | 3-methoxy-prop-2-yl | sec.-butyl | | |
| 338 | trimethylsilylethyl | sec.-butyl | | |
| 339 | 3-trimethylsilyl-propyl | sec.-butyl | | |
| 340 | 6-trimethylsilyl-hexyl | sec.-butyl | | |
| 341 | allyl | sec.-butyl | | |
| 342 | 3-methyl-but-2-en-yl | sec.-butyl | | |
| 343 | 1,5,9-trimethyl-deca-4,8-dienyl | sec.-butyl | | |
| 344 | propargyl | sec.-butyl | | |
| 345 | 4,4-dimethyl-but-yn-1-yl | sec.-butyl | | |
| 346 | cyclopentyl | sec.-butyl | | |
| 347 | 3-methyl-cyclopentyl | sec.-butyl | | |
| 348 | 3,3-dimethyl-cyclopentyl | sec.-butyl | | |
| 349 | 3,3,5-trimethyl-cyclopentyl | sec.-butyl | | |
| 350 | cyclohexyl | sec.-butyl | | |
| 351 | 3-methyl-cyclohexyl | sec.-butyl | | |

TABLE 1a-continued

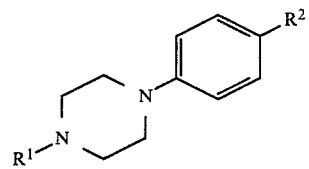

| Comp. no. | R¹ | R² | B.p. (°C./mbar) M.p. (°C.) | IR absorption (cm⁻¹) [Film] |
|---|---|---|---|---|
| 352 | 3,3-dimethyl-cyclohexyl | sec.-butyl | 55 | 2953, 2928, 2873, 2819, 1517, 1452, 1378, 1234 |
| 356 | 3,3,5-trimethyl-cyclohexyl | sec.-butyl | | |
| 354 | 3,3,5,5-tetramethyl-cyclohexyl | sec.-butyl | | |
| 355 | 3-ethyl-cyclohexyl | sec.-butyl | | |
| 356 | 3-ethyl-5-methyl-cyclohexyl | sec.-butyl | | |
| 357 | 4-methyl-cyclohexyl | sec.-butyl | | |
| 358 | 4-isopropyl-cyclohexyl | sec.-butyl | | |
| 359 | cycloheptyl | sec.-butyl | | |
| 360 | 4-hydroxy-cyclohexyl | sec.-butyl | | |
| 361 | 4-tert.-butoxy-cyclohexyl | sec.-butyl | | |
| 362 | 4-trimethylsilyl-cyclohexyl (cis/trans mixture) | sec.-butyl | | |
| 363 | cyclohex-2-en-yl | sec.-butyl | | |
| 364 | 4-tert.-butyl-cyclohexyl (isomer mixture) | sec.-butyl | | |
| 365 | trans-4-tert.-butyl-cyclohexyl | sec.-butyl | | |
| 366 | 4(2-methyl-but-2-yl)cyclohexyl (isomer mixture) | sec.-butyl | | |
| 367 | trans-4(2-methyl-but-2-yl)-cyclohexyl | sec.-butyl | | |
| 368 | 4(2,4,4-trimethyl-pent-2-yl)-cyclohexyl (isomer mixture) | sec.-butyl | | |
| 369 | trans-4(2,4,4-trimethyl-pent-2-yl)cyclohexyl | sec.-butyl | | |
| 370 | 4-hydroxy-3-methyl-cyclohexyl | sec.-butyl | | |
| 371 | 4-hydroxy-3,6-dimethyl-cyclohexyl | sec.-butyl | | |
| 372 | 4-hydroxy-3,3-dimethyl-cyclohexyl | sec.-butyl | | |
| 373 | 4-hydroxy-3,3,5-trimethyl-cyclohexyl | sec.-butyl | | |
| 374 | cyclohexylmethyl | sec.-butyl | | |
| 375 | cyclohexylethyl | sec.-butyl | | |
| 376 | 4-tert.-butyl-cyclohex-3-en-yl | sec.-butyl | | |
| 377 | 4-tert.-butyl-cyclohex-2-en-yl | sec.-butyl | | |
| 378 | 1-decalyl (cis/trans mixture) | sec.-butyl | | |
| 379 | 2-decalyl (cis/trans mixture) | sec.-butyl | | |
| 380 | trans-2-decalyl (eq/ax.-substituted) | sec.-butyl | | |
| 381 | eq.-trans-2-decalyl | sec.-butyl | | |
| 382 | 6-hydroxy-2-decalyl | sec.-butyl | | |
| 383 | 7-hydroxy-2-decalyl | sec.-butyl | | |
| 384 | 2-decalylmethyl | sec.-butyl | | |
| 385 | 9-methyl-trans-2-decalyl | sec.-butyl | | |
| 386 | 5,9-dimethyl-trans-2-decalyl | sec.-butyl | | |
| 387 | 5,5,9-trimethyl-trans-2-decalyl | sec.-butyl | | |
| 388 | 6-hydroxy-9-methyl-2-decalyl | sec.-butyl | | |
| 389 | 6-hydroxy-5,9-dimethyl-2-decalyl | sec.-butyl | | |
| 390 | 6-hydroxy-5,5,9-trimethyl-2-decalyl | sec.-butyl | | |
| 391 | tetrahydropyran-4-yl | sec.-butyl | | |
| 392 | tetrahydrothiopyran-4-yl | sec.-butyl | | |
| 393 | dioxan-2-yl-methyl | sec.-butyl | | |
| 394 | tetrahydropyran-2-yl-methyl | sec.-butyl | | |
| 395 | tetrahydropyran-3-yl-methyl | sec.-butyl | | |
| 396 | 3,5-dimethyl-dioxan-2-yl-methyl | sec.-butyl | | |
| 397 | 3,5-diethyl-dioxan-2-yl-methyl | sec.-butyl | | |
| 398 | 3,6-diethyl-dioxan-2-yl-methyl | sec.-butyl | | |
| 399 | 1,4-dioxa-spiro[4,5-decan]-8-yl | sec.-butyl | | |
| 400 | n-propyl | cyclohexyl | | |
| 401 | isopropyl | cyclohexyl | | |
| 402 | n-butyl | cyclohexyl | | |
| 403 | isobutyl | cyclohexyl | | |
| 404 | sec.-butyl | cyclohexyl | | |
| 405 | tert.-butyl | cyclohexyl | | |
| 406 | n-pentyl | cyclohexyl | | |
| 407 | 3-methyl-butyl | cyclohexyl | | |
| 408 | 2,2-dimethyl-propyl | cyclohexyl | | |
| 409 | pent-2-yl | cyclohexyl | | |

TABLE 1a-continued

| Comp. no. | R¹ | R² | B.p. (°C./mbar) M.p. (°C.) | IR absorption (cm⁻¹) [Film] |
|---|---|---|---|---|
| 410 | pent-3-yl | cyclohexyl | | |
| 411 | 1,2-dimethyl-propyl | cyclohexyl | | |
| 412 | n-hexyl | cyclohexyl | | |
| 413 | hex-2-yl | cyclohexyl | | |
| 414 | hex-3-yl | cyclohexyl | | |
| 415 | 1,2,2-trimethyl-propyl | cyclohexyl | | |
| 416 | 1,3-dimethyl-butyl | cyclohexyl | | |
| 417 | 4-methyl-pentyl | cyclohexyl | | |
| 418 | 3,3-dimethyl-butyl | cyclohexyl | oil | 2958, 2924, 2852, 2819, 1518, 1235, 1233, 829 |
| 419 | n-heptyl | cyclohexyl | | |
| 420 | hept-2-yl | cyclohexyl | | |
| 421 | hept-3-yl | cyclohexyl | | |
| 422 | hept-4-yl | cyclohexyl | | |
| 423 | diisopropyl-methyl | cyclohexyl | | |
| 424 | 1,4-dimethyl-pentyl | cyclohexyl | | |
| 425 | 4,4-dimethyl-pentyl | cyclohexyl | oil | 2953, 2925, 1517, 1448, 1364, 1251, 1241, 814 |
| 426 | 3,3-dimethyl-2-hydroxy-butyl | cyclohexyl | | |
| 427 | n-octyl | cyclohexyl | | |
| 428 | 2-methyl-hept-3-yl | cyclohexyl | | |
| 429 | 5-methyl-hept-3-yl | cyclohexyl | | |
| 430 | 5,5-dimethyl-hexyl | cyclohexyl | | |
| 431 | 2,4,4-trimethylpentyl | cyclohexyl | 56 | 2956, 2926, 2845, 1518, 1447, 1239, 1229, 814 |
| 432 | 6-methyl-hept-2-yl | cyclohexyl | | |
| 433 | n-nonyl | cyclohexyl | | |
| 434 | 2,5,5-trimethyl-hexyl | cyclohexyl | | |
| 435 | 2,6-dimethyl-hept-4-yl | cyclohexyl | | |
| 436 | 3,5,5-trimethyl-hexyl | cyclohexyl | | |
| 437 | n-decyl | cyclohexyl | | |
| 438 | 2,3,5,5-tetramethyl-hexyl | cyclohexyl | | |
| 439 | n-undecyl | cyclohexyl | | |
| 440 | n-dodecyl | cyclohexyl | | |
| 441 | n-tridecyl | cyclohexyl | | |
| 442 | 1,5,9-trimethyl-decyl | cyclohexyl | | |
| 443 | n-tetradecyl | cyclohexyl | | |
| 444 | 2-hydroxyethyl | cyclohexyl | | |
| 445 | 3-hydroxyethyl | Cyclohesyl | | |
| 446 | 4-hydroxy-butyl | cyclohexyl | | |
| 447 | 1-hydroxy-but-2-yl | cyclohexyl | | |
| 448 | 2-hydroxy-but-3-yl | cyclohexyl | | |
| 449 | 3-chloropropyl | cyclohexyl | | |
| 450 | 6-chlorohexyl | cyclohexyl | | |
| 451 | 5-chloropent-2-yl | cyclohexyl | | |
| 452 | 3-chlorobut-2-yl | cyclohexyl | | |
| 453 | 3,3-dichloro-prop-2-yl | cyclohexyl | | |
| 454 | 2-methoxyethyl | cyclohexyl | | |
| 455 | 2-ethoxyethyl | cyclohexyl | | |
| 456 | 2-tert.-butoxyethyl | cyclohexyl | | |
| 457 | 3-tert.-butoxy-ethyl | cyclohexyl | | |
| 458 | 6-methoxyhexyl | cyclohexyl | | |
| 459 | 3-methoxy-prop-2-yl | cyclohexyl | | |
| 460 | trimethylsilylethyl | cyclohexyl | | |
| 461 | 3-trimethylsilyl-propyl | cyclohexyl | | |
| 462 | 6-trimethylsilyl-hexyl | cyclohexyl | | |
| 463 | allyl | cyclohexyl | | |
| 464 | 3-methyl-but-2-en-yl | cyclohexyl | | |
| 465 | 1,5,9-trimethyl-deca-4,8-dienyl | cyclohexyl | | |
| 466 | propargyl | cyclohexyl | | |
| 467 | 4,4-dimethyl-but-yn-1-yl | cyclohexyl | | |
| 468 | cyclopentyl | cyclohexyl | | |
| 469 | 3-methyl-cyclopentyl | cyclohexyl | | |
| 470 | 3,3-dimethyl-cyclopentyl | cyclohexyl | | |
| 471 | 3,3,5-trimethyl-cyclopentyl | cyclohexyl | | |
| 472 | cyclohexyl | cyclohexyl | resin | |
| 473 | 3-methyl-cyclohexyl | cyclohexyl | | |
| 474 | 3,3-dimethyl-cyclohexyl | | oil | 2926, 2847, 1611, 1516, 1448, 1240, 1226, 1134, 815 |
| 475 | 3,3,5-trimethyl-cyclohexyl | cyclohexyl | | |
| 476 | 3,3,5,5-trimethyl-cyclohexyl | cyclohexyl | | |
| 477 | 3-ethyl-cyclohexyl | cyclohexyl | | |
| 478 | 3-ethyl-5-methyl-cyclohexyl | cyclohexyl | | |
| 479 | 4-methyl-cyclohexyl | cyclohexyl | | |
| 480 | 4-isopropyl-cyclohexyl | cyclohexyl | | |

TABLE 1a-continued

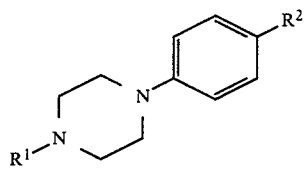

| Comp. no. | $R^1$ | $R^2$ | B.p. (°C./mbar) M.p. (°C.) | IR absorption (cm$^{-1}$) [Film] |
|---|---|---|---|---|
| 481 | cycloheptyl | cyclohexyl | | |
| 482 | 4-hydroxy-cyclohexyl | cyclohexyl | | |
| 483 | 4-tert.-butoxy-cyclohexyl | cyclohexyl | | |
| 484 | 4-trimethylsilylcyclohexyl (cis/trans mixture) | cyclohexyl | | |
| 485 | cyclohex-2-en-yl | cyclohexyl | | |
| 486 | 4-tert.-butyl-cyclohexyl (isomer mixture) | cyclohexyl | | |
| 487 | trans-4-tert.-butyl-cyclohexyl | cyclohexyl | | |
| 488 | 4(2-methyl-but-2-yl)cyclohexyl (isomer mixture) | cyclohexyl | | |
| 489 | trans-4(2-methyl-but-2-yl)-cyclohexyl | cyclohexyl | | |
| 490 | 4(2,4,4-trimethyl-pent-2-yl)-cyclohexyl (isomer mixture) | cyclohexyl | | |
| 491 | trans-4(2,4,4-trimethyl-pent-2-yl)cyclohexyl | cyclohexyl | | |
| 492 | 4-hydroxy-3-methyl-cyclohexyl | cyclohexyl | | |
| 493 | 4-hydroxy-3,6-dimethyl-cyclohexyl | cyclohexyl | | |
| 494 | 4-hydroxy-3,3-dimethyl-cyclohexyl | cyclohexyl | | |
| 495 | 4-hydroxy-3,3,5-trimethyl-cyclohexyl | cyclohexyl | | |
| 496 | cyclohexylmethyl | cyclohexyl | | |
| 497 | cyclohexylethyl | cyclohexyl | | |
| 498 | 4-tert.-butyl-cyclohex-3-en-yl | cyclohexyl | | |
| 499 | 4-tert.-butyl-cyclohex-2-en-yl | cyclohexyl | | |
| 500 | 1-decalyl (cis/trans mixture) | cyclohexyl | | |
| 501 | 2-Decalyl (cis/trans mixture) | cyclohexyl | | |
| 502 | trans-2-Decalyl (eq/ax.-substituted) | cyclohexyl | | |
| 503 | eq.-trans-2-decalyl | cyclohexyl | | |
| 504 | 6-hydroxy-2-decalyl | cyclohexyl | | |
| 505 | 7-hydroxy-2-decalyl | cyclohexyl | | |
| 506 | 2-decalylmethyl | cyclohexyl | | |
| 507 | 9-methyl-trans-2-decalyl | cyclohexyl | | |
| 508 | 5,9-dimethyl-trans-2-decalyl | cyclohexyl | | |
| 509 | 5,5,9-trimethyl-trans-2-decalyl | cyclohexyl | | |
| 510 | 6-hydroxy-9-methyl-2-decalyl | cyclohexyl | | |
| 511 | 6-hydroxy-5,9-dimethyl-2-decalyl | cyclohexyl | | |
| 512 | 6-hydroxy-5,5,9-trimethyl-2-decalyl | cyclohexyl | | |
| 513 | tetrahydropyran-4-yl | cyclohexyl | | |
| 514 | tetrahydrothiopyran-4-yl | cyclohexyl | | |
| 515 | dioxan-2-yl-methyl | cyclohexyl | | |
| 516 | tetrahydropyran-2-yl-methyl | cyclohexyl | | |
| 517 | tetrahydropyran-2-yl-methyl | cyclohexyl | | |
| 518 | 3,5-dimethyl-dioxan-2-yl-methyl | cyclohexyl | | |
| 519 | 3,5-diethyl-dioxan-2-yl-methyl | cyclohexyl | | |
| 520 | 3,6-diethyl-dioxan-2-yl-methyl | cyclohexyl | | |
| 521 | 3,3-dimethyl-butyl | tert.-butoxy | | |
| 522 | 4,4-dimethyl-pentyl | tert.-butoxy | | |
| 523 | 2,4,4-trimethyl-pentyl | tert.-butoxy | | |
| 524 | 3,3-dimethyl-cyclopentyl | tert.-butoxy | | |
| 525 | 3,3,5-trimethylcyclopentyl | tert.-butoxy | | |
| 526 | 3-methyl-cyclohexyl | tert.-butoxy | | |
| 527 | 3,3-dimethyl-cyclohexyl | tert.-butoxy | | |
| 528 | 3-ethyl-cyclohexyl | tert.-butoxy | | |
| 529 | 4-hydroxy-butyl | tert.-butoxy | | |
| 530 | 2-tert.-butoxy-ethyl | tert.-butoxy | | |
| 531 | 3-tert.-butoxy-propyl | tert.-butoxy | | |
| 532 | 4-hydroxy-cyclohexyl | tert.-butoxy | | |
| 533 | 4-hydroxy-3-methyl-cyclohexyl | tert.-butoxy | | |
| 534 | 4-hydroxy-3,3-dimethyl-cyclohexyl | tert.-butoxy | | |
| 535 | 3-ethyl-4-hydroxy-cyclohexyl | tert.-butoxy | | |

TABLE 1b

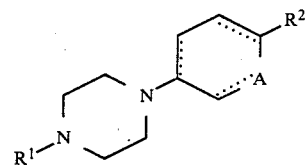

| Comp. no. | A | R$^1$ | R$^2$ | B.p.(°C./mbar) M.p.(°C.) | IR-Absorp.(cm$^{-1}$) (Film) |
|---|---|---|---|---|---|
| 536 | — | 3,3-dimethyl-butyl | tert.-butyl | | |
| 537 | — | 4,4-dimethyl-pentyl | tert.-butyl | | |
| 538 | — | 3,3-dimethyl-cyclopentyl | tert.-butyl | | |
| 539 | — | 3,3,5-trimethyl-cyclopentyl | tert.-butyl | | |
| 540 | — | 3-methyl-cyclohexyl | tert.-butyl | | |
| 541 | — | 3,3-dimethylcyclohexyl | tert.-butyl | | |
| 542 | — | 3-ethyl-cyclohexyl | tert.-butyl | | |
| 543a | CH$_2$ | n-propyl | tert.-butyl (cis-trans isomer mixt.) | | |
| 543b | CH$_2$ | n-propyl | tert.-butyl (trans isomer) | | |
| 544a | CH$_2$ | isopropyl | tert.-butyl (cis-trans isomer mixt.) | | |
| 544b | CH$_2$ | isopropyl | tert.-butyl (trans isomer) | | |
| 545a | CH$_2$ | n-butyl | tert.-butyl (cis-trans isomer mixt.) | | |
| 545b | CH$_2$ | n-butyl | tert.-butyl (trans isomer) | | |
| 546a | CH$_2$ | isobutyl | tert.-butyl (cis-trans isomer mixt.) | | |
| 546b | CH$_2$ | isobutyl | tert.-butyl (trans isomer) | | |
| 547a | CH$_2$ | sec.-butyl | tert.-butyl (cis-trans isomer mixt.) | | |
| 547b | CH$_2$ | sec.-butyl | tert.-butyl (trans isomer) | | |
| 548a | CH$_2$ | tert.-butyl | tert.-butyl (cis-trans isomer mixt.) | | |
| 548b | CH$_2$ | tert.-butyl | tert.-butyl (trans isomer) | | |
| 549a | CH$_2$ | n-pentyl | tert.-butyl (cis-trans isomer mixt.) | | |
| 549b | CH$_2$ | n-pentyl | tert.-butyl (trans isomer) | | |
| 550a | CH$_2$ | 3-methyl-butyl | tert.-butyl (cis-trans isomer mixt.) | oil | 2952, 2869, 2806, 2767, 1469, 1451, 1366, 1162 |
| 550b | CH$_2$ | 3-methyl-butyl | tert.-butyl (trans isomer) | | |
| 551a | CH$_2$ | 2,2-dimethyl-propyl | tert.-butyl (cis-trans isomer mixt.) | | |
| 551b | CH$_2$ | 2,2-dimethyl-propyl | tert.-butyl (trans isomer) | | |
| 552a | CH$_2$ | pent-2-yl | tert.-butyl (cis-trans isomer mixt.) | | |
| 552b | CH$_2$ | pent-2-yl | tert.-butyl (trans isomer) | | |
| 553a | CH$_2$ | 1,2-dimethyl-propyl | tert,-butyl (cis-trans isomer mixt.) | | |
| 553b | CH$_2$ | 1,2-dimethyl-propyl | tert.-butyl (trans isomer) | | |
| 554a | CH$_2$ | n-hexyl | tert-butyl (cis-trans isomer mixt.) | | |
| 554b | CH$_2$ | n-hexyl | tert.-butyl (trans isomer) | | |
| 555a | CH$_2$ | 1,2,2-trimethyl-propyl | tert.-butyl (cis-trans isomer mixt.) | | |
| 555b | CH$_2$ | 1,2,2-trimethyl-propyl | tert.-butyl (trans isomer) | | |
| 556a | CH$_2$ | 1,3-dimethyl-butyl | tert.-butyl (cis-trans isomer mixt.) | | |
| 556b | CH$_2$ | 1,3-dimethyl-butyl | tert.-butyl (trans isomer) | | |
| 557a | CH$_2$ | 4-methyl-pentyl | tert.-butyl (cis-trans isomer mixt.) | | |
| 557b | CH$_2$ | 4-methyl-pentyl | tert.-butyl (trans isomer) | | |
| 558a | CH$_2$ | 3,3-dimethyl-butyl | tert.-butyl (cis-trans isomer mixt.) | oil | 2953, 2867, 2805, 2765, 1471, 1445, 1364, 1152 |
| 558b | CH$_2$ | 3,3-dimethyl-butyl | tert.-butyl (trans isomer) | | |
| 559a | CH$_2$ | n-heptyl | tert.-butyl (cis-trans isomer mixt.) | | |
| 559a | CH$_2$ | n-heptyl | tert.-butyl (cis-trans isomer mixt.) | | |
| 559b | CH$_2$ | n-heptyl | tert.-butyl (trans isomer) | | |
| 560a | CH$_2$ | hept-2-yl | tert.-butyl (cis-trans isomer mixt.) | | |
| 560b | CH$_2$ | hept-2-yl | tert.-butyl (trans isomer) | | |
| 561a | CH$_2$ | diisopropyl-methyl | tert.-butyl (cis-trans isomer mixt.) | | |
| 561b | CH$_2$ | diisopropyl-methyl | tert.-butyl (trans isomer) | | |
| 562a | CH$_2$ | 1,4-dimethyl-pentyl | tert.-butyl (cis-trans isomer mixt.) | | |
| 562b | CH$_2$ | 1,4-dimethyl-pentyl | tert.-butyl (trans isomer) | | |
| 563a | CH$_2$ | 4,4-dimethyl-pentyl | tert.-butyl (cis-trans isomer mixt.) | | |
| 563b | CH$_2$ | 4,4-dimethyl-pentyl | tert.-butyl (trans isomer) | | |
| 564a | CH$_2$ | 3,3-dimethyl-2-hydroxybutyl | tert.-butyl (cis-trans isomer mixt.) | | |
| 564b | CH$_2$ | 3,3-dimethyl-2-hydroxybutyl | tert.-butyl (trans isomer) | | |
| 565a | CH$_2$ | n-octyl | tert.-butyl (cis-trans isomer mixt.) | | |
| 565b | CH$_2$ | n-octyl | tert.-butyl (trans isomer) | | |
| 566a | CH$_2$ | 2-methyl-hept-3-yl | tert.-butyl (cis-trans isomer mixt.) | | |
| 566b | CH$_2$ | 2-methyl-hept-3-yl | tert.-butyl (trans isomer) | | |
| 567a | CH$_2$ | 5-methyl-hept-3-yl | tert.-butyl (cis-trans isomer mixt.) | | |
| 567b | CH$_2$ | 5-methyl-hept-3-yl | tert.-butyl (trans isomer) | | |
| 568a | CH$_2$ | 5,5-dimethylhexyl | tert.-butyl (cis-trans isomer mixt.) | | |
| 568b | CH$_2$ | 5,5-dimethylhexyl | tert.-butyl (trans isomer) | | |
| 569a | CH$_2$ | 2,4,4,-trimethyl-pentyl | tert.-butyl (cis-trans isomer mixt.) | oil | 2950, 2867, 2807, 2767, 1476, 1467, 1457, 1365 |
| 569b | CH$_2$ | 2,4,4-trimethyl-pentyl | tert.-butyl (trans isomer) | | |
| 570a | CH$_2$ | 6-methyl-hept-2-yl | tert.-butyl (cis-trans isomer mixt.) | | |
| 570b | CH$_2$ | 6-methyl-hept-2-yl | tert.-butyl (trans isomer) | | |
| 571a | CH$_2$ | n-nonyl | tert.-butyl (cis-trans isomer mixt.) | | |
| 571b | CH$_2$ | n-nonyl | tert.-butyl (trans isomer) | | |
| 572a | CH$_2$ | 2,5,5-trimethyl-hexyl | tert.-butyl (cis-trans isomer mixt.) | | |
| 572b | CH$_2$ | 2,5,5-trimethyl-hexyl | tert.-butyl (trans isomer) | | |
| 573a | CH$_2$ | 2,6-dimethyl-hept-4-yl | tert.-butyl (cis-trans isomer mixt.) | | |

TABLE 1b-continued

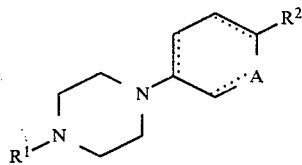

| Comp. no. | A | $R^1$ | $R^2$ | B.p.(°C./mbar) M.p.(°C.) | IR-Absorp.(cm$^{-1}$) (Film) |
|---|---|---|---|---|---|
| 573b | $CH_2$ | 2,6-dimethyl-hept-4-yl | tert.-butyl (trans isomer) | | |
| 574a | $CH_2$ | 3,5,5-trimethyl-hexyl | tert.-butyl (cis-trans isomer mixt.) | | |
| 574b | $CH_2$ | 3,5,5-trimethyl-hexyl | tert.-butyl (trans isomer) | | |
| 575a | $CH_2$ | n-decyl | tert.-butyl (cis-trans isomer mixt.) | | |
| 575b | $CH_2$ | n-decyl | tert.-butyl (trans isomer) | | |
| 576a | $CH_2$ | 2,3,5,5-tetramethyl-hexyl | tert.-butyl (cis-trans isomer mixt.) | | |
| 576b | $CH_2$ | 2,3,5,5-tetramethyl-hexyl | tert.-butyl (trans isomer) | | |
| 577a | $CH_2$ | n-undecyl | tert.-butyl (cis-trans isomer mixt.) | | |
| 577b | $CH_2$ | n-undecyl | tert.-butyl (trans isomer) | | |
| 578a | $CH_2$ | n-dodecyl | tert.-butyl (cis-trans isomer mixt.) | | |
| 578b | $CH_2$ | n-dodecyl | tert.-butyl (trans isomer) | | |
| 579a | $CH_2$ | n-tridecyl | tert.-butyl (cis-trans isomer mixt.) | | |
| 579b | $CH_2$ | n-tridecyl | tert.-butyl (trans isomer) | | |
| 580a | $CH_2$ | 1,5,9-trimethyl-decyl | tert.-butyl (cis-trans isomer mixt.) | | |
| 580b | $CH_2$ | 1,5,9-trimethyl-decyl | tert.-butyl (trans isomer) | | |
| 581a | $CH_2$ | n-tetradecyl | tert.-butyl (cis-trans isomer mixt.) | | |
| 581b | $CH_2$ | n-tetradecyl | tert.-butyl (trans isomer) | | |
| 582a | $CH_2$ | 2-hydroxyethyl | tert.-butyl (cis-trans isomer mixt.) | | |
| 582b | $CH_2$ | 2-hydroxyethyl | tert.-butyl (trans isomer) | | |
| 583a | $CH_2$ | 3-hydroxypropyl | tert.-butyl (cis-trans isomer mixt.) | | |
| 583b | $CH_2$ | 3-hydroxypropyl | tert.-butyl (trans isomer) | | |
| 584a | $CH_2$ | 4-hydroxy-butyl | tert.-butyl (cis-trans isomer mixt.) | | |
| 584b | $CH_2$ | 4-hydroxy-butyl | tert.-butyl (trans isomer) | | |
| 585a | $CH_2$ | 1-hydroxy-but-3-yl | tert.-butyl (cis-trans isomer mixt.) | | |
| 585b | $CH_2$ | 1-hydroxy-but-3-yl | tert.-butyl (trans isomer) | | |
| 586a | $CH_2$ | 2-hydroxy-but-3-yl | tert.-butyl (cis-trans isomer mixt.) | | |
| 586b | $CH_2$ | 2-hydroxy-but-3-yl | tert.-butyl (trans isomer) | | |
| 587a | $CH_2$ | 3-chloropropyl | tert.-butyl (cis-trans isomer mixt.) | | |
| 587b | $CH_2$ | 3-chloropropyl | tert.-butyl (trans isomer) | | |
| 588a | $CH_2$ | 6-chlorohexyl | tert.-butyl (cis-trans isomer mixt.) | | |
| 588b | $CH_2$ | 6-chlorohexyl | tert.-butyl (trans isomer) | | |
| 589a | $CH_2$ | 5-chloro-pent-2-yl | tert.-butyl (cis-trans isomer mixt.) | | |
| 589b | $CH_2$ | 5-chloro-pent-2-yl | tert.-butyl (trans isomer) | | |
| 590a | $CH_2$ | 3-chloro-but-2-yl | tert.-butyl (cis-trans isomer mixt.) | | |
| 590b | $CH_2$ | 3-chloro-but-2-yl | tert.-butyl (trans isomer) | | |
| 591a | $CH_2$ | 3,3-dichloro-prop-2-yl | tert.-butyl (cis-trans isomer mixt.) | | |
| 591b | $CH_2$ | 3,3-dichloro-prop-2-yl | tert.-butyl (trans isomer) | | |
| 592a | $CH_2$ | 2-methoxyethyl | tert.-butyl (cis-trans isomer mixt.) | | |
| 592b | $CH_2$ | 2-methoxyethyl | tert.-butyl (trans isomer) | | |
| 593a | $CH_2$ | 2-ethoxyethyl | tert.-butyl (cis-trans isomer mixt.) | | |
| 593b | $CH_2$ | 2-ethoxyethyl | tert.-butyl (trans isomer) | | |
| 594a | $CH_2$ | 2-tert.-butyoxyethyl | tert.-butyl (cis-trans isomer mixt.) | | |
| 594b | $CH_2$ | 2-tert.-butyoxyethyl | tert.-butyl (trans isomer) | | |
| 595a | $CH_2$ | 3-tert.-butyoxy-ethyl | tert.-butyl (cis-trans isomer mixt.) | | |
| 595b | $CH_2$ | 3-tert.-butyoxy-ethyl | tert.-butyl (trans isomer) | | |
| 596a | $CH_2$ | 6-methoxyhexyl | tert.-butyl (cis-trans isomer mixt.) | | |
| 596b | $CH_2$ | 6-methoxyhexyl | tert.-butyl (trans isomer) | | |
| 597a | $CH_2$ | 3-methoxy-prop-2-yl | tert.-butyl (cis-trans isomer mixt.) | | |
| 597b | $CH_2$ | 3-methoxy-prop-2-yl | tert.-butyl (trans isomer) | | |
| 598a | $CH_2$ | trimethylsilylethyl | tert.-butyl (cis-trans isomer mixt.) | | |
| 598b | $CH_2$ | trimethylsilylethyl | tert.-butyl (trans isomer) | | |
| 599a | $CH_2$ | 3-trimethylsilyl-propyl | tert.-butyl (cis-trans isomer mixt.) | | |
| 599b | $CH_2$ | 3-trimethylsilyl-propyl | tert.-butyl (trans isomer) | | |
| 600a | $CH_2$ | 6-trimethylsilyl-hexyl | tert.-butyl (cis-trans isomer mixt.) | | |
| 600b | $CH_2$ | 6-trimethylsilyl-hexyl | tert.-butyl (trans isomer) | | |
| 601a | $CH_2$ | allyl | tert.-butyl (cis-trans isomer mixt.) | | |
| 601b | $CH_2$ | allyl | tert.-butyl (trans isomer) | | |
| 602a | $CH_2$ | 3-methyl-but-2-en-yl | tert.-butyl (cis-trans isomer mixt.) | | |
| 602b | $CH_2$ | 3-methyl-but-2-en-yl | tert.-butyl (trans isomer) | | |
| 603a | $CH_2$ | 1,5,9-trimethyl-deca-4,8- | tert.-butyl (cis-trans isomer mixt.) | | |
| 603b | $CH_2$ | 1,5,9-trimethyl-deca-4,8- | tert.-butyl (trans isomer) | | |
| 604a | $CH_2$ | propargyl | tert.-butyl (cis-trans isomer mixt.) | | |
| 604b | $CH_2$ | propargyl | tert.-butyl (trans isomer) | | |
| 605a | $CH_2$ | 4,4-dimethyl-but-yn-1-yl | tert.-butyl (cis-trans isomer mixt.) | | |
| 605b | $CH_2$ | 4,4-dimethyl-but-yn-1-yl | tert.-butyl (trans isomer) | | |
| 606a | $CH_2$ | cyclopentyl | tert.-butyl (cis-trans isomer mixt.) | | |
| 606b | $CH_2$ | cyclopentyl | tert.-butyl (trans isomer) | | |
| 607a | $CH_2$ | 3-methyl-cyclopentyl | tert.-butyl (cis-trans isomer mixt.) | | |
| 607b | $CH_2$ | 3-methyl-cyclopentyl | tert.-butyl (trans isomer) | | |
| 608a | $CH_2$ | 3,3-dimethyl-cyclopentyl | tert.-butyl (cis-trans isomer mixt.) | | |
| 608b | $CH_2$ | 3,3-dimethyl-cyclopentyl | tert.-butyl (trans isomer) | | |
| 609a | $CH_2$ | 3,3,5-trimethyl-cyclopentyl | tert.-butyl (cis-trans isomer mixt.) | | |

TABLE 1b-continued

| Comp. no. | A | R¹ | R² | B.p.(°C./mbar) M.p.(°C.) | IR-Absorp.(cm⁻¹) (Film) |
|---|---|---|---|---|---|
| 609b | $CH_2$ | 3,3,5-trimethyl-cyclopentyl | tert.-butyl (trans isomer) | | |
| 610a | $CH_2$ | cyclohexyl | tert.-butyl (cis-trans isomer mixt.) | 75–78 | 2967, 2940, 2854, 2804, 2758, 1484, 1363, 1280, 1145 |
| 610b | $CH_2$ | cyclohexyl | tert.-butyl (trans isomer) | | |
| 611a | $CH_2$ | 3-methyl-cyclohexyl | tert.-butyl (cis-trans isomer mixt.) | | |
| 611b | $CH_2$ | 3-methyl-cyclohexyl | tert.-butyl (trans isomer) | | |
| 612a | $CH_2$ | 3,3-dimethyl-cyclohexyl | tert.-butyl (cis-trans isomer mixt.) | 90–92 | 2949, 2864, 2807, 1471, 1447, 1365, 1339, 1266, 1144 |
| 612b | $CH_2$ | 3,3-dimethyl-cyclohexyl | tert.-butyl (trans isomer) | | |
| 613a | $CH_2$ | 3,3,5-trimethyl-cyclohexyl | tert.-butyl (cis-trans isomer mixt.) | oil | 2945, 2864, 2836, 2804, 2764, 1467, 1452, 1365 |
| 613b | $CH_2$ | 3,3,5-trimethyl-cyclohexyl | tert.-butyl (trans isomer) | | |
| 614a | $CH_2$ | 3,3,5,5-tetramethyl-cyclohexyl | tert.-butyl (cis-trans isomer mixt.) | | |
| 614b | $CH_2$ | 3,3,5,5-tetramethyl-cyclohexyl | tert.-butyl (trans isomer) | | |
| 615a | $CH_2$ | 3-ethyl-cyclohexyl | tert.-butyl (cis-trans isomer mixt.) | | |
| 615b | $CH_2$ | 3-ethyl-cyclohexyl | tert.-butyl (trans isomer) | | |
| 616a | $CH_2$ | 3-ethyl-5-methyl-cyclohexyl | tert.-butyl (cis-trans isomer mixt.) | | |
| 616b | $CH_2$ | 3-ethyl-5-methyl-cyclohexyl | tert.-butyl (trans isomer) | | |
| 617a | $CH_2$ | 4-methyl-cyclohexyl | tert.-butyl (cis-trans isomer mixt.) | | |
| 617b | $CH_2$ | 4-methyl-cyclohexyl | tert.-butyl (trans isomer) | | |
| 618a | $CH_2$ | 4-isopropyl-cyclohexyl | tert.-butyl (cis-trans isomer mixt.) | | |
| 618b | $CH_2$ | 4-isopropyl-cyclohexyl | tert.-butyl (trans isomer) | | |
| 619a | $CH_2$ | cycloheptyl | tert.-butyl (cis-trans isomer mixt.) | | |
| 619b | $CH_2$ | cycloheptyl | tert.-butyl (trans isomer) | | |
| 620a | $CH_2$ | 4-hydroxy-cyclohexyl | tert.-butyl (cis-trans isomer mixt.) | | |
| 620b | $CH_2$ | 4-hydroxy-cyclohexyl | tert.-butyl (trans isomer) | | |
| 621a | $CH_2$ | 4-tert.-butoxy-cyclohexyl | tert.-butyl (cis-trans isomer mixt.) | | |
| 621b | $CH_2$ | 4-tert.-butoxy-cyclohexyl | tert.-butyl (trans isomer) | | |
| 622a | $CH_2$ | 4-trimethylsolyl-cyclohexyl | tert.-butyl (cis-trans isomer mixt.) | | |
| 622b | $CH_2$ | 4-trimethylsolyl-cyclohexyl | tert.-butyl (trans isomer) | | |
| 623a | $CH_2$ | cyclohex-2-en-yl | tert.-butyl (cis-trans isomer mixt.) | | |
| 623b | $CH_2$ | cyclohex-2-en-ylo | tert.-butyl (trans isomer) | | |
| 624a | $CH_2$ | 4-tert.-butyl-cyclohexyl | tert.-butyl (cis-trans isomer mixt.) | 145–47 | 2965, 2940, 2862, 2800, 2761, 1454, 1145, 1366, 1278, 1146 |
| 624b | $CH_2$ | 4-tert.-butyl-cyclohexyl | tert.-butyl (trans isomer) | | |
| 625a | $CH_2$ | trans-4-tert.-butyl-cyclohexyl | tert.-butyl (cis-trans isomer mixt.) | | |
| 625b | $CH_2$ | trans-4-tert.-butyl-cyclohexyl | tert.-butyl (trans isomer) | | |
| 626a | $CH_2$ | 4(2-methyl-but-2-yl)cyclohexyl | tert.-butyl (cis-trans isomer mixt.) | | |
| 626b | $CH_2$ | 4(2-methyl-but-2-yl)cyclohexyl | tert.-butyl (trans isomer) | | |
| 627a | $CH_2$ | trans-4(2-methyl-but-2-yl)-cyclohexyl | tert.-butyl (cis-trans isomer mixt.) | | |
| 627b | $CH_2$ | trans-4(2-methyl-but-2-yl)-cyclohexyl | tert.-butyl (trans isomer) | | |
| 628a | $CH_2$ | 4(2,4,4-trimethyl-pent-2-yl)-cyclohexyl | tert.-butyl (cis-trans isomer mixt.) | | |
| 628b | $CH_2$ | 4(2,4,4-trimethyl-pent-2-yl)-cyclohexyl | tert.-butyl (trans isomer) | | |
| 629a | $CH_2$ | trans-4(2,4,4-trimethyl-pent-2-yl)cyclohexyl | tert.-butyl (cis-trans isomer mixt.) | | |
| 629b | $CH_2$ | trans-4(2,4,4-trimethyl-pent-2-yl)cyclohexyl | tert.-butyl (trans isomer) | | |
| 630a | $CH_2$ | 4-hydroxy-3-methyl-cyclohexyl | tert.-butyl (cis-trans isomer mixt.) | | |
| 630b | $CH_2$ | 4-hydroxy-3-methyl-cyclohexyl | tert.-butyl (trans isomer) | | |
| 631a | $CH_2$ | 4-hydroxy-3,6-dimethyl-cyclohexyl | tert.-butyl (cis-trans isomer mixt.) | | |
| 631b | $CH_2$ | 4-hydroxy-3,6-dimethyl-cyclohexyl | tert.-butyl (trans isomer) | | |
| 632a | $CH_2$ | 4-hydroxy-3,3-dimethyl-cyclohexyl | tert.-butyl (cis-trans isomer mixt.) | | |
| 632b | $CH_2$ | 4-hydroxy-3,3-dimethyl-cyclohexyl | tert.-butyl (trans isomer) | | |

TABLE 1b-continued

[Structure: piperazine with R¹-N and N connected to cyclohexyl ring bearing R² and A]

| Comp. no. | A | R¹ | R² | B.p.(°C./mbar) M.p.(°C.) | IR-Absorp.(cm⁻¹) (Film) |
|---|---|---|---|---|---|
| 633a | $CH_2$ | 4-hydroxy-3,3,5-trimethyl-cyclohexyl | tert.-butyl (cis-trans isomer mixt.) | | |
| 633b | $CH_2$ | 4-hydroxy-3,3,5-trimethyl-cyclohexyl | tert.-butyl (trans isomer) | | |
| 634a | $CH_2$ | cyclohexylmethyl | tert.-butyl (cis-trans isomer mixt.) | | |
| 634b | $CH_2$ | cyclohexylmethyl | tert.-butyl (trans isomer) | | |
| 635a | $CH_2$ | cyclohexylethyl | tert.-butyl (cis-trans isomer mixt.) | | |
| 635b | $CH_2$ | cyclohexylethyl | tert.-butyl (trans isomer) | | |
| 636a | $CH_2$ | 4-tert.-butyl-cyclohex-3-en-yl | tert.-butyl (cis-trans isomer mixt.) | | |
| 636b | $CH_2$ | 4-tert.-butyl-cyclohex-3-en-yl | tert.-butyl (trans isomer) | | |
| 637a | $CH_2$ | 4-tert.-butyl-cyclohex-2-en-yl | tert.-butyl (cis-trans isomer mixt.) | | |
| 637b | $CH_2$ | 4-tert.-butyl-cyclohex-2-en-yl | tert.-butyl (trans isomer) | | |
| 638a | $CH_2$ | 1-decalyl | tert.-butyl (cis-trans isomer mixt.) | | |
| 638b | $CH_2$ | 1-decalyl | tert.-butyl (trans isomer) | | |
| 639a | $CH_2$ | 2-decalyl | tert.-butyl (cis-trans isomer mixt.) | resin | 2923, 2858, 1467, 1449, 1365, 1339, 1158 |
| 639b | $CH_2$ | 2-decalyl | tert.-butyl (trans isomer) | | |
| 640a | $CH_2$ | trans-2-decalyl | tert.-butyl (cis-trans isomer mixt.) | | |
| 640b | $CH_2$ | trans-2-decalyl | tert.-butyl (trans isomer) | | |
| 641a | $CH_2$ | eq.-trans-2-decalyl | tert.-butyl (cis-trans isomer mixt.) | | |
| 641b | $CH_2$ | eq.-trans-2-decalyl | tert.-butyl (trans isomer) | | |
| 642a | $CH_2$ | 6-hydroxy-2-decalyl | tert.-butyl (cis-trans isomer mixt.) | | |
| 642b | $CH_2$ | 6-hydroxy-2-decalyl | tert.-butyl (trans isomer) | | |
| 643a | $CH_2$ | 7-hydroxy-2-decalyl | tert.-butyl (cis-trans isomer mixt.) | | |
| 643b | $CH_2$ | 7-hydroxy-2-decalyl | tert.-butyl (trans isomer) | | |
| 644a | $CH_2$ | 2-decalylmethyl | tert.-butyl (cis-trans isomer mixt.) | | |
| 644b | $CH_2$ | 2-decalylmethyl | tert.-butyl (trans isomer) | | |
| 645a | $CH_2$ | 9-methyl-trans-2-decalyl | tert.-butyl (cis-trans isomer mixt.) | | |
| 645b | $CH_2$ | 9-methyl-trans-2-decalyl | tert.-butyl (trans isomer) | | |
| 646a | $CH_2$ | 5,9-dimethyl-trans-2-decalyl | tert.-butyl (cis-trans isomer mixt.) | | |
| 646b | $CH_2$ | 5,9-dimethyl-trans-2-decalyl | tert.-butyl (trans isomer) | | |
| 647a | $CH_2$ | 5,5,9-trimethyl-trans-2-decalyl | tert.-butyl (cis-trans isomer mixt.) | | |
| 647b | $CH_2$ | 5,5,9-trimethyl-trans-2-decalyl | tert.-butyl (trans isomer) | | |
| 648a | $CH_2$ | 6-hydroxy-9-methyl-2-decalyl | tert.-butyl (cis-trans isomer mixt.) | | |
| 648b | $CH_2$ | 6-hydroxy-9-methyl-2-decalyl | | | |
| 649a | $CH_2$ | 6-hydroxy-5,9-dimethyl-2-decalyl | tert.-butyl (trans isomer) | | |
| 649b | $CH_2$ | 6-hydroxy-5,9-dimethyl-2-decalyl | tert.-butyl (cis-trans isomer mixt.) | | |
| 650a | $CH_2$ | 6-hydroxy-5,5,9-trimethyl-2-decalyl | tert.-butyl (trans isomer) | | |
| 650b | $CH_2$ | 6-hydroxy-5,5,9-trimethyl-2-decalyl | tert.-butyl (cis-trans isomer mixt.) | | |
| 651a | $CH_2$ | tetrahydropyran-4-yl | tert.-butyl (cis-trans isomer mixt.) | | |
| 651b | $CH_2$ | tetrahydropyran-4-yl | tert.-butyl (trans isomer) | | |
| 652a | $CH_2$ | tetrahydrothiopyran-4-yl | tert.-butyl (cis-trans isomer mixt.) | | |
| 652b | $CH_2$ | tetrahydrothiopyran-4-yl | tert.-butyl (trans isomer) | | |
| 653a | $CH_2$ | dioxan-2-yl-methyl | tert.-butyl (cis-trans isomer mixt.) | | |
| 653b | $CH_2$ | dioxan-2-yl-methyl | tert.-butyl (trans isomer) | | |
| 654a | $CH_2$ | tetrahydropyran-2-yl-methyl | tert.-butyl (cis-trans isomer mixt.) | | |
| 654b | $CH_2$ | tetrahydropyran-2-yl-methyl | tert.-butyl (trans isomer) | | |
| 655a | $CH_2$ | tetrahydropyran-3-yl-methyl | tert.-butyl (cis-trans isomer mixt.) | | |
| 655b | $CH_2$ | tetrahydropyran-3-yl-methyl | tert.-butyl (trans isomer) | | |
| 656a | $CH_2$ | 3,5-dimethyl-dioxan-2-yl-methyl | tert.-butyl (cis-trans isomer mixt.) | | |
| 656b | $CH_2$ | 3,5-dimethyl-dioxan-2-yl-methyl | tert.-butyl (trans isomer) | | |
| 657a | $CH_2$ | 3,5-diethyl-dioxan-2-yl-methyl | tert.-butyl (cis-trans isomer mixt.) | | |
| 657b | $CH_2$ | 3,5-diethyl-dioxan-2-yl-methyl | tert.-butyl (trans isomer) | | |
| 658a | $CH_2$ | 3,6-diethyl-dioxan-2-yl- | tert.-butyl (cis-trans isomer mixt.) | | |

TABLE 1b-continued

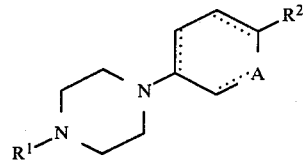

| Comp. no. | A | R¹ | R² | B.p.(°C./mbar) M.p.(°C.) | IR-Absorp.(cm⁻¹) (Film) |
|---|---|---|---|---|---|
| 658b | CH₂ | 3,6-diethyl-dioxan-2-yl-methyl | tert.-butyl (trans isomer) | | |
| 659a | CH₂ | 1,4-dioxa-spiro[4,5-decan]-8-yl | tert.-butyl (cis-trans isomer mixt.) | | |
| 659b | CH₂ | 1,4-dioxa-spiro[4,5-decan]-8-yl | tert.-butyl (trans isomer) | | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

Some of the novel compounds have a very good action on human-pathogenic fungi, such as Trichophyton mentagrophytes and Candida albicans.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 17 is mixed with 10 parts by weight of N-methyl-α-pyrrolidone. A mixture is obtained which is suitable for application in the form of very fine drops.

II. 20 parts by weight of compound no. 85 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 558a is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 612a is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 17 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 85 is intimately mixed with 97 parts by weight of particulate kaolin. A dust is obtained containing 3% by weight of the active ingredient.

VII. 30 parts by weight of compound no. 558a is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 612a is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 17 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
 ferric dimethyldithiocarbamate,
 zinc dimethyldithiocarbamate,
 zinc ethylenebisdithiocarbamate,
 manganese ethylenebisdithiocarbamate,
 manganese zinc ethylenediaminebisdithiocarbamate,
 tetramethylthiuram disulfides,
 ammonia complex of zinc N,N'-ethylenebisdithiocarbamate,
 ammonia complex of zinc N,N'-propylenebisdithiocarbamate,
 zinc N,N'-propylenebisdithiocarbamate and N,N'-polypropylenebis(thiocarbamyl) disulfide;
nitro derivatives, such as
 dinitro(1-methylheptyl)-phenyl crotonate,
 2-sec-butyl-4,6-dinitrophenyl 3,3-dimethylacrylate,
 2-sec-butyl-4,6-dinitrophenyl isopropylcarbonate and
 diisopropyl 5-nitroisophthalate;
heterocyclic substances, such as
 2-heptadecylimidazol-2-yl acetate,
 2,4-dichloro-6-(o-chloroanilino)-s-triazine,
 0,0-diethyl phthalimidophosphonothioate,
 5-amino-1-[-bis-(dimethylamino)-phosphinyl]-3-phenyl-1,2,4-triazole,
 2,3-dicyano-1,4-dithioanthraquinone,
 2-thio-1,3-dithio[4,5-b]quinoxaline,
 methyl 1-(butylcarbamyl)-2-benzimidazolecarbamate,
 2-methoxycarbonylaminobenzimidazole,
 2-(fur-2-yl)-benzimidazole,
 2-(thiazol-4-yl)benzimidazole,
 N-(1,1,2,2-tetrachloroethylthio)-tetrahydrophthalimide,
 N-trichloromethylthiotetrahydrophthalimide,
 N-trichloromethylthiophthalimide,
 N-dichlorofluoromethylthio-N',N'-dimethyl-N-phenylsulfuric acid diamide,
 5-ethoxy-3-trichloromethyl-1,2,3-thiadiazole,
 2-thiocyanatomethylthiobenzothiazole,
 1,4-dichloro-2,5-dimethoxybenzene,
 4-(2-chlorophenylhydrazono)-3-methyl-5-isoxazolone,
 2-thiopyridine 1-oxide,
 8-hydroxyquinoline and its copper salt,
 2,3-dihydro-5-carboxanilido-6-methyl-1,4-oxathiyne,
 2,3-dihydro-5-carboxanilido-6-methyl-1,4-oxathiyne 4,4-dioxide,
 2-methyl-5,6-dihydro-4H-pyran-3-carboxanilide,
 2-methylfuran-3-carboxanilide,
 2,5-dimethylfuran-3-carboxanilide,
 2,4,5-trimethylfuran-3-carboxanilide,
 2,5-dimethyl-N-cyclohexylfuran-3-carboxamide,
 N-cyclohexyl-N-methoxy-2,5-diethylfuran-3-carboxamide,
 2-methylbenzanilide,
 2-iodobenzanilide,
 N-formyl-N-morpholine-2,2,2-trichloroethylacetal,
 piperazine-1,4-diylbis-(1-(2,2,2-trichloroethyl)-formamide),
 1-(3,4-dichloroanilino)-1-formylamino-2,2,2-trichloroethane,
 2,6-dimethyl-N-tridecylmorpholine and its salts,
 2,6-dimethyl-N-cyclododecylmorpholine and its salts,
 N-[3-(p-tert.-butylphenyl)-2-methylpropyl]-cis-2,6-dimethylmorpholine,
 N-[3-(p-tert.-butylphenyl)-2-methylpropyl]-piperidine,
 1-[2-(2,4-dichlorophenyl)-4-ethyl-1,3-dioxolan-2-ylethyl]-1H-1,2,4-triazole,
 1-[2-(2,4-dichlorophenyl)-4-n-propyl-1,3-dioxolan-2-ylethyl]-1H-1,2,4-triazole,
 N-(n-propyl)-N-(2,4,6-trichlorophenoxyethyl)-N'-imidazolyl-urea,
 1-(4-chlorophenoxy)-3,3-dimethyl-1-(1H-1,2,4-triazol-1-yl)-butan-2-one,
 1-(4-chlorophenoxy)-3,3-dimethyl-1-(1H-1,2,4-triazol-1-yl)-butan-2-ol,
 1-(4-phenylphenoxy)-3,3-dimethyl-1-(1H-1,2,4-triazol-1-yl)-2-butanol,
 α-(2-chlorophenyl)-α-(4-chlorophenyl)-5-pyrimidinemethanol, 5-butyl-(2-dimethylamino-4-hydroxy-6-methyl-pyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, N-methyl-N'-3-(p-tert-butylphenyl)-2-methylpropylpiperazine (A) disclosed in DE 2,727,482 was employed.

USE EXAMPLE 1

Action on cucumber mildew

Leaves of pot-grown cucumber seedlings of the "Chinesische Schlange" variety were sprayed at the two-leaf stage with a spore suspension of cucumber mildew. After about 20 hours, these plants were sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 70 to 80%. The extent of fungus spread was determined 21 days after inoculation.

The results show that active ingredients 17, 24, 25, 83, 87, 96, 107, 111, 217, 219, 231, 558a, 569a, 610a, 612a, 624a and 639a have, when applied as 0.025 wt % spray liquors, a better fungicidal action (98%) than prior art active ingredient A applied as a 0.1% spray liquor (80%).

USE EXAMPLE 2

Action on wheat brown rust

Leaves of pot-grown wheat seedlings of the "Frühgold" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 3, 4, 17, 24, 42, 60, 83, 85, 91, 96, 107, 111, 131, 151, 158, 167, 217, 219, 231, 293, 352, 418, 431, 474, 550a, 558a, 569a, 610a, 612a, 619a, 624a and 639a have, when applied as 0.025 wt % spray liquors, a better fungicidal action (98%) than prior art active ingredient A (60%).

USE EXAMPLE 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 3, 60, 85, 107, 111, 151, 219, 474, 558a, 569a, 610a, 612a and 639a have, when applied as 0.05% spray liquors, a better fungicidal action (97%) than prior art active ingredient A (60%) applied as a 0.1% spray liquor.

USE EXAMPLE 4

Action on *Botrytis cinerea* in paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results show that active ingredients 85, 91, 111, 217, 231, 472, 474, 486 and 639a have, when applied as 0.05% spray liquors, a better fungicidal action (94%) than prior art active ingredient A (10%).

We claim:

1. N,N'-disubstituted piperazines of the formula I

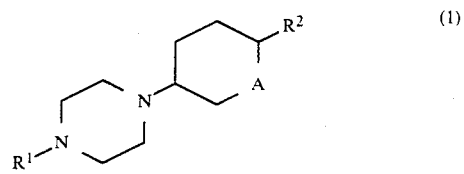

where the group is unsaturated (=) or saturated (—) and the substituents $R^1$, $R^2$ and A have the following meanings:

A is —, —CH=, —CH$_2$—, —CH$_2$—CH$_2$—, $R^1$ is $C_2$–$C_{20}$-alkyl, $C_3$–$C_{20}$-alkenyl, $C_3$–$C_{20}$-alkenyl, $C_3$–$C_{20}$-alkynyl, $C_4$–$C_{12}$-cycloalkyl, $C_4$–$C_{12}$-cycloalkenyl, $C_4$–$C_{20}$-alkylcycloalkyl, $C_4$–$C_{20}$-cycloalkenylalkyl, $C_4$–$C_{20}$-alkylcycloalkenyl, $C_9$–$C_{11}$-bicycloalkyl, $C_{10}$–$C_{15}$-bicycloalkylalkyl or $C_{10}$–$C_{15}$-alkylbicycloalkyl, wherein each of these radicals may be unsubstituted or substituted by hydroxy, 1 to 3 halogen atoms, $C_1$–$C_5$-alkoxy or $C_3$–$C_9$-trialkylsilyl, $R^1$ is further 5- or 7-membered heterocycloalkyl with 1 or 2 heteroatoms selected from the group consisting of oxygen and sulfur, 5 to 7-membered heterocycloalkylmethyl with 1 or 2 heteroatoms selected from the group consisting of oxygen and sulfur, $C_1$–$C_8$-alkylsubstituted 5- to 7-membered heterocycloalkylmethyl with 1 or 2 heteroatoms selected from the group consisting of oxygen and sulfur, and $R^2$ is branched $C_3$–$C_{10}$-alkyl, branched $C_3$–$C_8$-alkoxy, trimethylsilyl, $C_3$–$C_7$-cycloalkyl, $C_3$–$C_8$-alkylthio, or plant-physiologically tolerated salts thereof.

2. A fungicide containing an N,N'-disubstituted piperazine of the formula I

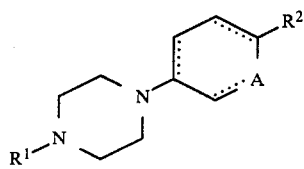

where the group $\cdots$ is unsaturated (=) or saturated (—) and the substituents $R^1$, $R^2$ and A have the following meanings:

A is —, —CH=, —CH$_2$—, —CH$_2$—CH$_2$—, $R^1$ is $C_2$–$C_{20}$-alkyl, $C_3$–$C_{20}$-alkenyl, $C_3$–$C_{20}$-alkynyl, $C_4$–$C_{12}$-cycloalkyl, $C_4$–$C_{12}$-cycloalkenyl, $C_4$–$C_{20}$-alkylcycloalkyl, $C_4$–$C_{20}$-cycloalkenylalkyl, $C_4$–$C_{20}$-alkylcycloalkenyl, $C_9$–$C_{11}$-bicycloalkyl, $C_{10}$–$C_{15}$-bicycloalkylalkyl or $C_{10}$–$C_{15}$-alkylbicycloalkyl, wherein each of these radicals may be substituted or substituted by hydroxy, 1 to 3 halogen atoms, $C_1$–$C_5$-alkoxy or $C_3$–$C_9$-trialkylsilyl, $R^1$ is further 5- to 7-membered heterocycloalkyl with 1 or 2 heteroatoms selected from the group consisting of oxygen and sulfur, 5 to 7-membered heterocycloalkylmethyl with 1 or 2 heteroatoms selected from the group consisting of oxygen and sulfur, $C_1$–$C_8$-alkyl-substituted 5- to 7-membered heterocycloalkylmethyl with 1 or 2 heteroatoms selected from the group consisting of oxygen and sulfur, and $R^2$ is branched $C_3$–$C_{10}$-alkyl, branched $C_3$–$C_8$-alkoxy, trimethylsilyl, $C_3$–$C_7$-cycloalkyl, $C_3$–$C_8$-alkylthio, or a plant-physiologically tolerated salt thereof, and conventional carriers.

3. A process for combating fungi, wherein the fungi, or the materials, plants, seed or soil threatened by fungus attack are treated with an N,N'-disubstituted piperazine of the formula I

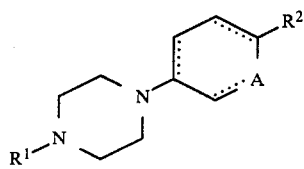

where the group $\cdots$ is unsaturated (=) or saturated (—) and the substituents $R^1$, $R^2$ and A have the following meanings:

A is —, —CH=, —CH$_2$—, —CH$_2$—CH$_2$—, $R^1$ is $C_2$–$C_{20}$-alkyl, $C_3$–$C_{20}$-alkenyl, $C_3$–$C_{20}$-alkynyl, $C_4$–$C_{12}$-cycloalkyl, $C_4$–$C_{12}$-cycloalkenyl, $C_4$–$C_{20}$-alkylcycloalkyl, $C_4$–$C_{20}$-cycloalkenylalkyl, $C_4$–$C_{20}$-alkylcycloalkenyl, $C_9$–$C_{11}$-bicycloalkyl, $C_{10}$–$C_{15}$-bicycloalkylalkyl or $C_{10}$–$C_{15}$-alkylbicycloalkyl, wherein each of radicals may be unsubstituted or substituted by hydroxy, 1 to 3 halogen atoms, $C_1$–$C_5$-alkoxy or $C_3$–$C_9$-trialkylsilyl, $R^1$ is further 5- to 7-membered heterocycloalkyl with 1 or 2 heteroatoms selected from the group consisting of oxygen and sulfur, 5 to 7-membered heterocycloalkylmethyl with 1 or 2 heteroatoms selected from the group consisting of oxygen and sulfur, $C_1$–$C_8$-alkyl-substituted 5- to 7-membered heterocycloalkylmethyl with 1 or 2 heteroatoms selected from the group consisting of oxygen and sulfur, and $R^2$ is branched $C_3$–$C_{10}$-alkyl, branched $C_3$–$C_8$-alkoxy, trimethylsilyl, $C_3$–$C_7$-cycloalkyl, $C_3$–$C_8$-alkylthio, or a plant-physiologically tolerated salt thereof.

4. A compound as set forth in claim 1, where the group $\cdots$ is unsaturated (=), A is the group —CH=, $R^1$ is 3,3-dimethylcyclohexyl, and $R^2$ is tert-butyl.

5. A compound as set forth in claim 1, where the group $\cdots$ is saturated (—), A is the group —CH$_2$—, $R^1$ is 3,3-dimethylcyclohexyl, and $R^2$ is tert-butyl.

6. A compound as set forth in claim 1, where the group $\cdots$ is unsaturated (=), A is the group —CH$_2$—, $R^1$ is 3,3-dimethylbutyl, and $R^2$ is tert-butyl.

7. A compound as set forth in claim 1, where the group $\cdots$ is saturated (—), A is the group —CH$_2$—, $R^1$ is 3,3-dimethylbutyl, and $R^2$ is tert-butyl.

* * * * *